(12) United States Patent
Felton et al.

(10) Patent No.: US 12,232,878 B1
(45) Date of Patent: Feb. 25, 2025

(54) ATRIAL FIBRILLATION USER INTERFACES

(71) Applicant: Apple Inc., Cupertino, CA (US)

(72) Inventors: Nicholas Felton, Sunnyvale, CA (US);
Heather E. Daniel, San Jose, CA (US);
Vera Carr, San Francisco, CA (US);
Patrick Okechukwu Eronini, Jr.,
Mountain View, CA (US); Eamon
Francis Gilravi, San Francisco, CA
(US); Ruchi Goswami, Sunnyvale, CA
(US); Ava Baunoo Rezvani, Los Gatos,
CA (US); David Tsay, Cupertino, CA
(US)

(73) Assignee: Apple Inc., Cupertino, CA (US)

( * ) Notice: Subject to any disclaimer, the term of this patent is extended or adjusted under 35 U.S.C. 154(b) by 479 days.

(21) Appl. No.: 17/389,260

(22) Filed: Jul. 29, 2021

Related U.S. Application Data

(60) Provisional application No. 63/060,022, filed on Aug. 1, 2020.

(51) Int. Cl.
A61B 5/361 (2021.01)
A61B 5/00 (2006.01)
A61B 5/339 (2021.01)
G16H 10/60 (2018.01)

(52) U.S. Cl.
CPC ............ *A61B 5/361* (2021.01); *A61B 5/0006* (2013.01); *A61B 5/339* (2021.01); *A61B 5/7475* (2013.01); *G16H 10/60* (2018.01); *A61B 2560/02* (2013.01)

(58) Field of Classification Search
CPC ....... A61B 5/361; A61B 5/0006; A61B 5/339; A61B 5/7475; A61B 2560/02; A61B 5/349; A61B 5/346; A61B 5/318; A61B 5/24; A61B 5/746; A61B 2560/0242; G16H 10/60
See application file for complete search history.

(56) References Cited

U.S. PATENT DOCUMENTS

| 4,205,628 A | 6/1980 | Null |
| 4,842,266 A | 6/1989 | Sweeney et al. |
| 5,423,863 A | 6/1995 | Felblinger et al. |
| 5,458,548 A | 10/1995 | Crossing et al. |
| 5,474,077 A | 12/1995 | Suga |
| 5,642,731 A | 7/1997 | Kehr |
| 5,788,655 A | 8/1998 | Yoshimura et al. |

(Continued)

FOREIGN PATENT DOCUMENTS

| AU | 2013201390 B2 * | 5/2015 | ........... G06F 3/0481 |
| CN | 103191557 A | 7/2013 | |

(Continued)

OTHER PUBLICATIONS

Corrected Notice of Allowance received for U.S. Appl. No. 17/197,628, mailed on Jul. 29, 2022, 2 pages.

(Continued)

*Primary Examiner* — Paula J Stice
(74) *Attorney, Agent, or Firm* — DLA Piper LLP (US)

(57) ABSTRACT

The present disclosure generally relates to displaying atrial fibrillation data. A computer system concurrently displays a first representation of atrial fibrillation data for a first period of time and a first representation of non-heart data the first period of time.

57 Claims, 22 Drawing Sheets

(56) References Cited

U.S. PATENT DOCUMENTS

| | | |
|---|---|---|
| 6,013,008 A | 1/2000 | Fukushima |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,244,988 B1 | 6/2001 | Delman |
| 6,302,789 B2 | 10/2001 | Harada et al. |
| 6,416,471 B1 | 7/2002 | Kumar et al. |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee |
| 6,866,613 B1 | 3/2005 | Brown et al. |
| 7,020,514 B1 | 3/2006 | Wiesel |
| 7,111,157 B1 | 9/2006 | Hooper |
| 7,251,454 B2 | 7/2007 | White |
| 7,302,272 B2 | 11/2007 | Ackley |
| 7,313,435 B2 | 12/2007 | Nakada et al. |
| 7,662,065 B1 | 2/2010 | Kahn et al. |
| 7,695,406 B2 | 4/2010 | Waters |
| 7,739,148 B2 | 6/2010 | Suzuki et al. |
| 7,771,320 B2 | 8/2010 | Riley et al. |
| 8,060,229 B2 | 11/2011 | Gupta et al. |
| 8,105,208 B2 | 1/2012 | Oleson et al. |
| 8,152,694 B2 | 4/2012 | Srinivasan et al. |
| 8,200,323 B2 | 6/2012 | Dibenedetto et al. |
| 8,321,006 B1 | 11/2012 | Snyder et al. |
| 8,341,557 B2 | 12/2012 | Pisula et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,784,115 B1 | 7/2014 | Chuang |
| 8,825,445 B2 | 9/2014 | Hoffman et al. |
| 8,934,963 B1 | 1/2015 | Farazi |
| 8,990,006 B1 | 3/2015 | Wallace et al. |
| 9,011,292 B2 | 4/2015 | Weast et al. |
| 9,020,538 B1 | 4/2015 | White et al. |
| 9,026,927 B2 | 5/2015 | Brumback et al. |
| 9,230,076 B2 | 1/2016 | King et al. |
| 9,557,881 B1 | 1/2017 | Jain et al. |
| 9,801,562 B1 | 10/2017 | Host-Madsen |
| 9,813,642 B1 | 11/2017 | Chen et al. |
| 9,854,653 B1 | 12/2017 | Ackmann et al. |
| 10,056,006 B1 | 8/2018 | Hsu-Hoffman et al. |
| 10,175,781 B2 | 1/2019 | Karagozler et al. |
| 10,220,258 B2 | 3/2019 | Gu et al. |
| 10,226,195 B2 | 3/2019 | Briante et al. |
| 10,339,830 B2 | 7/2019 | Han et al. |
| 10,398,381 B1 | 9/2019 | Heneghan et al. |
| 10,437,962 B2 | 10/2019 | Soni et al. |
| 10,568,533 B2 | 2/2020 | Soli et al. |
| 10,685,090 B2 | 6/2020 | Petterson et al. |
| 10,736,543 B2 | 8/2020 | Chen et al. |
| 11,073,942 B2 | 7/2021 | Lee et al. |
| 11,107,569 B1 | 8/2021 | Devoto |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2004/0017300 A1 | 1/2004 | Kotzin et al. |
| 2004/0236189 A1 | 11/2004 | Hawthorne et al. |
| 2005/0010117 A1 | 1/2005 | Agutter et al. |
| 2005/0113650 A1 | 5/2005 | Pacione et al. |
| 2005/0124324 A1 | 6/2005 | Thomas et al. |
| 2005/0165627 A1 | 7/2005 | Fotsch et al. |
| 2006/0052727 A1 | 3/2006 | Palestrant |
| 2006/0098109 A1 | 5/2006 | Ooki |
| 2006/0149144 A1 | 7/2006 | Lynn et al. |
| 2006/0152372 A1 | 7/2006 | Stout |
| 2006/0160090 A1 | 7/2006 | Macina et al. |
| 2006/0184800 A1 | 8/2006 | Rosenberg |
| 2006/0195039 A1* | 8/2006 | Drew ............... G16H 40/67 600/523 |
| 2006/0235319 A1 | 10/2006 | Belohlavek et al. |
| 2006/0240959 A1 | 10/2006 | Huang |
| 2006/0250524 A1 | 11/2006 | Roche |
| 2007/0032733 A1 | 2/2007 | Burton |
| 2007/0033069 A1 | 2/2007 | Rao et al. |
| 2007/0071256 A1 | 3/2007 | Ito |
| 2007/0143433 A1 | 6/2007 | Daigle |
| 2007/0169614 A1 | 7/2007 | Sasaki et al. |
| 2007/0249949 A1 | 10/2007 | Hadley |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0077073 A1* | 3/2008 | Keenan ............... A61M 5/142 604/19 |
| 2008/0082145 A1 | 4/2008 | Skwarek et al. |
| 2008/0096726 A1 | 4/2008 | Riley et al. |
| 2008/0161161 A1 | 7/2008 | Pipinich et al. |
| 2008/0161707 A1 | 7/2008 | Farringdon et al. |
| 2008/0229226 A1 | 9/2008 | Rowbottom et al. |
| 2008/0240519 A1 | 10/2008 | Nagamitsu |
| 2008/0254767 A1 | 10/2008 | Jin |
| 2008/0300110 A1 | 12/2008 | Smith et al. |
| 2009/0007017 A1 | 1/2009 | Anzures et al. |
| 2009/0012988 A1 | 1/2009 | Brown |
| 2009/0170532 A1 | 7/2009 | Lee et al. |
| 2009/0222056 A1 | 9/2009 | Lindh et al. |
| 2009/0259134 A1 | 10/2009 | Levine |
| 2010/0003951 A1 | 1/2010 | Ray et al. |
| 2010/0010832 A1 | 1/2010 | Boute et al. |
| 2010/0017489 A1 | 1/2010 | Birnbaum et al. |
| 2010/0060586 A1 | 3/2010 | Pisula et al. |
| 2010/0062905 A1 | 3/2010 | Rottler et al. |
| 2010/0064255 A1 | 3/2010 | Rottler et al. |
| 2010/0076331 A1 | 3/2010 | Chan et al. |
| 2010/0125306 A1* | 5/2010 | McCabe ............... A61B 5/1104 607/9 |
| 2010/0137106 A1 | 6/2010 | Oshima et al. |
| 2010/0145209 A1 | 6/2010 | Lee et al. |
| 2010/0145220 A1 | 6/2010 | van Vliet |
| 2010/0264097 A1 | 10/2010 | Sun et al. |
| 2010/0298899 A1 | 11/2010 | Donnelly et al. |
| 2011/0032105 A1 | 2/2011 | Hoffman et al. |
| 2011/0071869 A1 | 3/2011 | Obrien et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0159469 A1 | 6/2011 | Hwang et al. |
| 2011/0167369 A1 | 7/2011 | van Os |
| 2011/0230169 A1 | 9/2011 | Ohki |
| 2011/0245623 A1 | 10/2011 | Chutani et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2012/0015778 A1 | 1/2012 | Lee et al. |
| 2012/0015779 A1 | 1/2012 | Powch et al. |
| 2012/0029303 A1 | 2/2012 | Shaya |
| 2012/0034897 A1 | 2/2012 | Kreitzer et al. |
| 2012/0038651 A1 | 2/2012 | Case et al. |
| 2012/0041767 A1 | 2/2012 | Hoffman et al. |
| 2012/0042039 A1 | 2/2012 | Mark |
| 2012/0059664 A1 | 3/2012 | Georgiev et al. |
| 2012/0065480 A1 | 3/2012 | Badilini et al. |
| 2012/0116550 A1 | 5/2012 | Hoffman et al. |
| 2012/0150759 A1 | 6/2012 | Tarjan |
| 2012/0159380 A1 | 6/2012 | Kocienda et al. |
| 2012/0179319 A1 | 7/2012 | Gilman et al. |
| 2012/0232414 A1 | 9/2012 | Mollicone et al. |
| 2012/0245447 A1 | 9/2012 | Karan et al. |
| 2012/0283587 A1 | 11/2012 | Gosh et al. |
| 2012/0283855 A1 | 11/2012 | Hoffman et al. |
| 2012/0290109 A1 | 11/2012 | Engelberg et al. |
| 2012/0302843 A1 | 11/2012 | Otsubo et al. |

(56) References Cited

U.S. PATENT DOCUMENTS

| | | |
|---|---|---|
| 2013/0054150 A1 | 2/2013 | Sacks et al. |
| 2013/0054720 A1 | 2/2013 | Kang et al. |
| 2013/0065569 A1 | 3/2013 | Leipzig et al. |
| 2013/0067050 A1 | 3/2013 | Kotteri et al. |
| 2013/0114100 A1 | 5/2013 | Torii et al. |
| 2013/0138734 A1 | 5/2013 | Crivello et al. |
| 2013/0158367 A1 | 6/2013 | Pacione et al. |
| 2013/0158416 A1* | 6/2013 | Hatlestad ............ A61B 5/0031 600/484 |
| 2013/0185097 A1 | 7/2013 | Saria et al. |
| 2013/0215042 A1 | 8/2013 | Messerschmidt et al. |
| 2013/0215119 A1 | 8/2013 | Vanhoecke |
| 2013/0231711 A1 | 9/2013 | Kaib |
| 2013/0231947 A1 | 9/2013 | Shusterman |
| 2013/0263719 A1 | 10/2013 | Watterson et al. |
| 2013/0317380 A1 | 11/2013 | Liley et al. |
| 2013/0324210 A1 | 12/2013 | Doig et al. |
| 2013/0325358 A1 | 12/2013 | Oshima et al. |
| 2013/0330694 A1 | 12/2013 | Watterson |
| 2014/0037107 A1 | 2/2014 | Marino et al. |
| 2014/0039840 A1 | 2/2014 | Yuen et al. |
| 2014/0081118 A1 | 3/2014 | Reinhold et al. |
| 2014/0089836 A1 | 3/2014 | Damani et al. |
| 2014/0108998 A1 | 4/2014 | Chaudhri et al. |
| 2014/0142403 A1 | 5/2014 | Brumback et al. |
| 2014/0143678 A1 | 5/2014 | Mistry et al. |
| 2014/0173521 A1 | 6/2014 | Mayor |
| 2014/0176335 A1 | 6/2014 | Brumback et al. |
| 2014/0176475 A1 | 6/2014 | Myers et al. |
| 2014/0180786 A1 | 6/2014 | Sullivan |
| 2014/0200691 A1 | 7/2014 | Lee et al. |
| 2014/0240349 A1 | 8/2014 | Tuukkanen |
| 2014/0266776 A1 | 9/2014 | Miller et al. |
| 2014/0274413 A1 | 9/2014 | Chelst |
| 2014/0275854 A1 | 9/2014 | Venkatraman et al. |
| 2014/0278220 A1 | 9/2014 | Yuen |
| 2014/0288390 A1 | 9/2014 | Hong et al. |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0337041 A1 | 11/2014 | Madden et al. |
| 2014/0358473 A1 | 12/2014 | Goel et al. |
| 2014/0358584 A1 | 12/2014 | Worden et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0058263 A1 | 2/2015 | Landers |
| 2015/0065095 A1 | 3/2015 | Seo et al. |
| 2015/0067513 A1 | 3/2015 | Zambetti et al. |
| 2015/0073285 A1 | 3/2015 | Albert et al. |
| 2015/0081060 A1 | 3/2015 | Hwang et al. |
| 2015/0081210 A1 | 3/2015 | Yeh et al. |
| 2015/0081529 A1 | 3/2015 | Lee et al. |
| 2015/0099991 A1 | 4/2015 | Yamaguchi et al. |
| 2015/0113553 A1 | 4/2015 | Pan |
| 2015/0124067 A1 | 5/2015 | Bala et al. |
| 2015/0130830 A1 | 5/2015 | Nagasaki et al. |
| 2015/0164349 A1 | 6/2015 | Gopalakrishnan et al. |
| 2015/0180746 A1 | 6/2015 | Day et al. |
| 2015/0181314 A1 | 6/2015 | Swanson |
| 2015/0185967 A1 | 7/2015 | Ly et al. |
| 2015/0196804 A1 | 7/2015 | Koduri et al. |
| 2015/0205930 A1 | 7/2015 | Shaanan et al. |
| 2015/0216448 A1 | 8/2015 | Lotan et al. |
| 2015/0220883 A1 | 8/2015 | Bfar et al. |
| 2015/0251053 A1 | 9/2015 | Hoffman et al. |
| 2015/0269848 A1 | 9/2015 | Yuen et al. |
| 2015/0288944 A1 | 10/2015 | Nistico et al. |
| 2015/0297134 A1 | 10/2015 | Albert et al. |
| 2015/0343709 A1 | 12/2015 | Gerstle et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0058313 A1 | 3/2016 | Sato |
| 2016/0058336 A1 | 3/2016 | Blahnik et al. |
| 2016/0062572 A1 | 3/2016 | Yang et al. |
| 2016/0062582 A1 | 3/2016 | Wilson et al. |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0107031 A1 | 4/2016 | Palatsi et al. |
| 2016/0109961 A1 | 4/2016 | Parshionikar |
| 2016/0132046 A1 | 5/2016 | Beoughter et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0174857 A1 | 6/2016 | Eggers et al. |
| 2016/0196635 A1 | 7/2016 | Cho et al. |
| 2016/0210099 A1 | 7/2016 | Hampapuram et al. |
| 2016/0220225 A1 | 8/2016 | Wang et al. |
| 2016/0235325 A1 | 8/2016 | Chou |
| 2016/0235374 A1 | 8/2016 | Miller et al. |
| 2016/0246880 A1 | 8/2016 | Battiah et al. |
| 2016/0249857 A1 | 9/2016 | Choi et al. |
| 2016/0249864 A1 | 9/2016 | Kang et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0275990 A1 | 9/2016 | Vassort |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0292373 A1 | 10/2016 | Spors et al. |
| 2016/0299769 A1 | 10/2016 | Hunter et al. |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0302717 A1 | 10/2016 | Tawa et al. |
| 2016/0328736 A1 | 11/2016 | Wang et al. |
| 2016/0346607 A1 | 12/2016 | Rapfogel |
| 2016/0360100 A1 | 12/2016 | Kim et al. |
| 2016/0371464 A1 | 12/2016 | Bricker |
| 2016/0375306 A1 | 12/2016 | Gu et al. |
| 2017/0000359 A1 | 1/2017 | Kohli et al. |
| 2017/0001073 A1 | 1/2017 | Krueger et al. |
| 2017/0007159 A1 | 1/2017 | Dieffenderfer et al. |
| 2017/0007167 A1 | 1/2017 | Kostic et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0046024 A1 | 2/2017 | Dascola et al. |
| 2017/0053542 A1* | 2/2017 | Wilson .................... G09B 5/02 |
| 2017/0065224 A1 | 3/2017 | Rahko et al. |
| 2017/0075551 A1 | 3/2017 | Robinson et al. |
| 2017/0086693 A1 | 3/2017 | Peterson et al. |
| 2017/0091567 A1 | 3/2017 | Wang et al. |
| 2017/0095695 A1 | 4/2017 | Mangusson et al. |
| 2017/0127997 A1 | 5/2017 | Hyde et al. |
| 2017/0143262 A1 | 5/2017 | Kurunmäki et al. |
| 2017/0172522 A1 | 6/2017 | Insler et al. |
| 2017/0188841 A1 | 7/2017 | Ma et al. |
| 2017/0202496 A1 | 7/2017 | Ramanathan |
| 2017/0239524 A1 | 8/2017 | Lee et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0293727 A1 | 10/2017 | Klaassen et al. |
| 2017/0300186 A1 | 10/2017 | Kuhar et al. |
| 2017/0301039 A1 | 10/2017 | Dyer et al. |
| 2017/0303844 A1 | 10/2017 | Baker et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0337033 A1 | 11/2017 | Duyan et al. |

(56) References Cited

U.S. PATENT DOCUMENTS

| | | |
|---|---|---|
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0049659 A1 | 2/2018 | Briante et al. |
| 2018/0049696 A1 | 2/2018 | Eom et al. |
| 2018/0053200 A1 | 2/2018 | Cronin et al. |
| 2018/0060522 A1 | 3/2018 | Petterson et al. |
| 2018/0064356 A1 | 3/2018 | Mendenhall et al. |
| 2018/0065025 A1 | 3/2018 | Toda et al. |
| 2018/0074464 A1 | 3/2018 | Essery et al. |
| 2018/0078182 A1 | 3/2018 | Chen et al. |
| 2018/0137937 A1 | 5/2018 | Gass et al. |
| 2018/0140903 A1 | 5/2018 | Poure et al. |
| 2018/0189077 A1 | 7/2018 | Gupta et al. |
| 2018/0206766 A1 | 7/2018 | Blahnik et al. |
| 2018/0272190 A1 | 9/2018 | Miura et al. |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0089701 A1 | 3/2019 | Mercury et al. |
| 2019/0184234 A1 | 6/2019 | Packles et al. |
| 2019/0209777 A1 | 7/2019 | O'connell et al. |
| 2019/0232111 A1 | 8/2019 | Williams et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0279520 A1 | 9/2019 | Wilson et al. |
| 2019/0336827 A1 | 11/2019 | Intonato et al. |
| 2019/0339849 A1 | 11/2019 | Williams et al. |
| 2019/0342616 A1 | 11/2019 | Domm et al. |
| 2019/0387982 A1 | 12/2019 | Buller |
| 2020/0014967 A1 | 1/2020 | Putnam |
| 2020/0098278 A1 | 3/2020 | Doti et al. |
| 2020/0101365 A1 | 4/2020 | Wilson et al. |
| 2020/0356242 A1 | 11/2020 | Wilson et al. |
| 2021/0110908 A1 | 4/2021 | Blahnik et al. |
| 2021/0113137 A1 | 4/2021 | Soli et al. |
| 2021/0191584 A1 | 6/2021 | Williams et al. |
| 2021/0255826 A1 | 8/2021 | Devine et al. |
| 2022/0047918 A1 | 2/2022 | Williams et al. |
| 2023/0101625 A1 | 3/2023 | Soli et al. |
| 2023/0136700 A1 | 5/2023 | Williams et al. |
| 2023/0389806 A1 | 12/2023 | Felton et al. |
| 2024/0050016 A1 | 2/2024 | Soli et al. |

FOREIGN PATENT DOCUMENTS

| | | |
|---|---|---|
| CN | 104720765 A | 6/2015 |
| CN | 105320454 A | 2/2016 |
| CN | 105980008 A | 9/2016 |
| CN | 106164808 A | 11/2016 |
| CN | 106371816 A | 2/2017 |
| CN | 106537397 A | 3/2017 |
| CN | 106725384 A | 5/2017 |
| CN | 106901720 A | 6/2017 |
| CN | 107278138 A | 10/2017 |
| CN | 107361755 A | 11/2017 |
| CN | 107454831 A | 12/2017 |
| CN | 107591211 A | 1/2018 |
| CN | 107713981 A | 2/2018 |
| EP | 2529663 A1 | 12/2012 |
| EP | 2993602 A1 | 3/2016 |
| EP | 3042606 A1 | 7/2016 |
| EP | 3117767 A1 | 1/2017 |
| JP | 5-288869 A | 11/1993 |
| JP | 2004-174006 A | 6/2004 |
| JP | 3635663 B2 | 4/2005 |
| JP | 2007-330513 A | 12/2007 |
| JP | 2008-11865 A | 1/2008 |
| JP | 2009-78134 A | 4/2009 |
| JP | 2010-182287 A | 8/2010 |
| JP | 2012-35071 A | 2/2012 |
| JP | 2012-86088 A | 5/2012 |
| JP | 2012-174055 A | 9/2012 |
| JP | 2013-530776 A | 8/2013 |
| JP | 2014-168685 A | 9/2014 |
| JP | 2015-73590 A | 4/2015 |
| JP | 2016-158867 A | 9/2016 |
| JP | 2016-185288 A | 10/2016 |
| KR | 10-2012-0098854 A | 9/2012 |
| KR | 10-2012-0132732 A | 12/2012 |
| KR | 10-2013-0056646 A | 5/2013 |
| KR | 10-2013-0097235 A | 9/2013 |
| KR | 10-2015-0026635 A | 3/2015 |
| KR | 10-2015-0062761 A | 6/2015 |
| KR | 10-1594486 B1 | 2/2016 |
| KR | 10-2016-0027943 A | 3/2016 |
| KR | 10-2016-0105129 A | 9/2016 |
| KR | 10-2016-0142418 A | 12/2016 |
| KR | 10-2017-0003608 A | 1/2017 |
| KR | 10-2017-0029014 A | 3/2017 |
| KR | 10-2017-0032471 A | 3/2017 |
| WO | 97/38626 A1 | 10/1997 |
| WO | 2005/029242 A2 | 3/2005 |
| WO | 2006/046648 A1 | 5/2006 |
| WO | 2010/047035 A1 | 4/2010 |
| WO | 2011/072111 A2 | 6/2011 |
| WO | 2012/060588 A2 | 5/2012 |
| WO | 2013/103570 A1 | 7/2013 |
| WO | 2013/169870 A1 | 11/2013 |
| WO | 2015/089484 A1 | 6/2015 |
| WO | 2015/131065 A1 | 9/2015 |
| WO | 2015/153803 A1 | 10/2015 |
| WO | 2015/187799 A1 | 12/2015 |
| WO | 2016/022203 A1 | 2/2016 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/207745 A1 | 12/2016 |
| WO | 2017/003045 A1 | 1/2017 |
| WO | 2017/062621 A1 | 4/2017 |
| WO | 2017/087642 A1 | 5/2017 |
| WO | 2017/090810 A1 | 6/2017 |

OTHER PUBLICATIONS

Notice of Allowance received for Chinese Patent Application No. 202010618569.X, mailed on Jan. 7, 2022, 2 pages (1 page of English Translation and 1 page of Official Copy).

Office Action received for Chinese Patent Application No. 202011220489.5, mailed on Dec. 1, 2021, 19 pages (11 pages of English Translation and 8 pages of Official Copy).

Notice of Allowance received for U.S. Appl. No. 16/143,997, mailed on Sep. 30, 2021, 8 pages.

Notice of Allowance received for Korean Patent Application No. 10-2022-7017918, mailed on Jun. 13, 2022, 6 pages (2 pages of English Translation and 4 pages of Official Copy).

Notice of Allowance received for U.S. Appl. No. 17/197,628, mailed on Jun. 24, 2022, 8 pages.

Office Action received for Chinese Patent Application No. 202010618240.3, mailed on May 25, 2022, 20 pages (11 pages of English Translation and 9 pages of Official Copy).

Notice of Allowance received for Japanese Patent Application No. 2021-167557, mailed on Jan. 27, 2023, 4 pages (1 page of English Translation and 3 pages of Official Copy).

Office Action received for Australian Patent Application No. 2021261861, mailed on Oct. 14, 2022, 5 pages.

Office Action received for Chinese Patent Application No. 202010618240.3, mailed on Sep. 21, 2022, 16 pages (9 pages of English Translation and 7 pages of Official Copy).

(56) References Cited

OTHER PUBLICATIONS

Office Action received for Danish Patent Application No. PA202070395, mailed on Oct. 7, 2022, 4 pages.
Decision to Grant received for European Patent Application No. 20180592.6, mailed on Sep. 1, 2022, 3 pages.
Brief Communication Regarding Oral Proceedings received for European Patent Application No. 20180581.9, mailed on Nov. 30, 2021, 1 page.
Brief Communication regarding Oral Proceedings received for European Patent Application No. 20180592.6, mailed on Dec. 21, 2021, 1 page.
Office Action received for Chinese Patent Application No. 202010618240.3, mailed on Dec. 3, 2021, 23 pages (14 pages of English Translation and 9 pages of Official Copy).
Office Action received for Danish Patent Application No. PA202070395, mailed on Dec. 15, 2021, 5 pages.
Notice of Acceptance received for Australian Patent Application No. 2022235614, mailed on Jul. 6, 2023, 3 pages.
Office Action received for Danish Patent Application No. PA202070395, mailed on Jul. 5, 2023, 6 pages.
Brief Communication Regarding Oral Proceedings received for European Patent Application No. 18727543.3, mailed on Mar. 23, 2023, 1 page.
Office Action received for Danish Patent Application No. PA202070395, mailed on Mar. 31, 2023, 3 pages.
Result of Consultation received for European Patent Application No. 18727543.3, mailed on Mar. 15, 2023, 6 pages.
Office Action received for Australian Patent Application No. 2021204422, mailed on May 31, 2022, 2 pages.
Office Action received for Chinese Patent Application No. 202011220489.5, mailed on Apr. 25, 2022, 15 pages (9 pages of English Translation and 6 pages of Official Copy).
Corrected Notice of Allowance received for U.S. Appl. No. 17/135,710, mailed on Aug. 18, 2023, 4 pages.
Decision to Grant received for European Patent Application No. 18727543.3, mailed on Aug. 18, 2023, 2 pages.
Examiner Interview Summary received for U.S. Appl. No. 17/896,791, mailed on Sep. 1, 2023, 2 pages.
Non-Final Office Action received for U.S. Appl. No. 17/896,791, mailed on Aug. 30, 2023, 11 pages.
Notice of Acceptance received for Australian Patent Application No. 2021204422, mailed on Aug. 15, 2022, 3 pages.
Office Action received for Japanese Patent Application No. 2021-167557, mailed on Aug. 15, 2022, 5 pages (3 pages of English Translation and 2 pages of Official Copy).
Extended European Search Report received for European Patent Application No. 22190169.7, mailed on Nov. 23, 2022, 11 pages.
Office Action received for Japanese Patent Application No. 2021-153558, mailed on Nov. 21, 2022, 8 pages (4 pages of English Translation and 4 pages of Official Copy).
Office Action received for Korean Patent Application No. 10-2022-7031866, mailed on Nov. 18, 2022, 11 pages (5 pages of English Translation and 6 pages of Official Copy).
Notice of Allowance received for U.S. Appl. No. 17/135,710, mailed on Jul. 27, 2023, 9 pages.
Office Action received for Australian Patent Application No. 2019234289, mailed on Nov. 1, 2021, 4 pages.
Office Action received for Korean Patent Application No. 10-2021-7031939, mailed on Oct. 19, 2021, 11 pages (5 pages of English Translation and 6 pages of Official Copy).
Corrected Notice of Allowance received for U.S. Appl. No. 17/197,628, mailed on Apr. 27, 2022, 3 pages.
Intention to Grant received for European Patent Application No. 20180592.6, mailed on Apr. 20, 2022, 21 pages.
Intention to Grant received for European Patent Application No. 18727543.3, mailed on Apr. 12, 2023, 9 pages.
Corrected Notice of Allowance received for U.S. Appl. No. 16/143,997, mailed on Nov. 16, 2021, 2 pages.
Office Action received for Australian Patent Application No. 2021261861, mailed on Jan. 12, 2023, 4 pages.

Decision to Refuse received for European Patent Application No. 20180581.9, mailed on Apr. 13, 2022, 16 pages.
Minutes of the Oral Proceedings received for European Patent Application No. 20180581.9, mailed on Apr. 13, 2022, 10 pages.
Minutes of the Oral Proceedings received for European Patent Application No. 20180592.6, mailed on Apr. 7, 2022, 10 pages.
Notice of Allowance received for Korean Patent Application No. 10-2021-7031939, mailed on Apr. 5, 2022, 4 pages (1 page of English Translation and 3 pages of Official Copy).
Office Action received for Chinese Patent Application No. 201880032190.1, mailed on Nov. 14, 2022, 23 pages (12 pages of English Translation and 11 pages of Official Copy).
Notice of Allowance received for U.S. Appl. No. 17/197,628, mailed on Mar. 23, 2022, 35 pages.
Summons to Attend Oral Proceedings received for European Patent Application No. 18727543.3, mailed on Oct. 25, 2022, 8 pages.
Notice of Allowance received for Japanese Patent Application No. 2021-153558, mailed on Jun. 9, 2023, 4 pages (1 page of English Translation and 3 pages of Official Copy).
Office Action received for Chinese Patent Application No. 201880032190.1, mailed on May 31, 2023, 20 pages (12 pages of English Translation and 8 pages of Official Copy).
Notice of Allowance received for Japanese Patent Application No. 2020-153166, mailed on Sep. 13, 2021, 4 pages (1 page of English Translation and 3 pages of Official Copy).
Office Action received for Chinese Patent Application No. 202010618569.X, mailed on Sep. 7, 2021, 7 pages (4 pages of English Translation and 3 pages of Official Copy).
Notice of Allowance received for Japanese Patent Application No. 2019-563407, mailed on Aug. 20, 2021, 4 pages (1 page of English Translation and 3 pages of Official Copy).
Brief Communication Regarding Oral Proceedings received for European Patent Application No. 20180581.9, mailed on Jan. 26, 2022, 1 page.
Brief Communication regarding Oral Proceedings received for European Patent Application No. 20180592.6, mailed on Jan. 26, 2022, 2 pages.
Result of Consultation received for European Patent Application No. 20180581.9, mailed on Jan. 21, 2022, 14 pages.
Result of Consultation received for European Patent Application No. 20180592.6, mailed on Jan. 26, 2022, 18 pages.
Advisory Action received for U.S. Appl. No. 16/143,909, mailed on Nov. 7, 2019, 5 pages.
Advisory Action received for U.S. Appl. No. 16/143,997, mailed on Dec. 26, 2019, 7 pages.
Applicant-Initiated Interview Summary received for U.S. Appl. No. 16/143,997, mailed on Aug. 13, 2020, 3 pages.
Applicant-Initiated Interview Summary received for U.S. Appl. No. 16/144,735, mailed on Jun. 18, 2020, 3 pages.
Applicant-Initiated Interview Summary received for U.S. Appl. No. 16/144,753, mailed on Jun. 18, 2020, 3 pages.
Applicant-Initiated Interview Summary received for U.S. Appl. No. 15/705,849, mailed on Feb. 14, 2020, 3 pages.
Applicant-Initiated Interview Summary received for U.S. Appl. No. 15/705,849, mailed on Jun. 29, 2020, 3 pages.
Applicant-Initiated Interview Summary received for U.S. Appl. No. 16/143,997, mailed on May 3, 2021, 4 pages.
Applicant-Initiated Interview Summary received for U.S. Appl. No. 16/144,753, mailed on Nov. 4, 2020, 3 pages.
Certificate of Examination received for Australian Patent Application No. 2019100222, mailed on Aug. 29, 2019, 2 pages.
Corrected Notice of Allowance received for U.S. Appl. No. 16/143,909, mailed on Feb. 20, 2020, 3 pages.
Corrected Notice of Allowance received for U.S. Appl. No. 16/143,909, mailed on Mar. 18, 2020, 3 pages.
Corrected Notice of Allowance received for U.S. Appl. No. 16/143,959, mailed on Dec. 13, 2019, 2 pages.
Corrected Notice of Allowance received for U.S. Appl. No. 16/143,997, mailed on Jul. 2, 2021, 2 pages.
Corrected Notice of Allowance received for U.S. Appl. No. 16/143,997, mailed on Jun. 4, 2021, 2 pages.
Decision to Grant received for Danish Patent Application No. PA201870600, mailed on Oct. 17, 2019, 2 pages.

(56) References Cited

OTHER PUBLICATIONS

Decision to Grant received for Danish Patent Application No. PA201870601, mailed on Aug. 17, 2020, 2 pages.
Decision to Grant received for Danish Patent Application No. PA201870602, mailed on Aug. 18, 2020, 2 pages.
Extended European Search Report received for European Patent Application No. 20180581.9, mailed on Aug. 12, 2020, 9 pages.
Extended European Search Report received for European Patent Application No. 20180592.6, mailed on Aug. 11, 2020, 10 pages.
Final Office Action received for U.S. Appl. No. 15/705,849, mailed on May 1, 2020, 17 pages.
Final Office Action received for U.S. Appl. No. 16/143,909, mailed on Aug. 28, 2019, 20 pages.
Final Office Action received for U.S. Appl. No. 16/143,997, mailed on Feb. 9, 2021, 16 pages.
Final Office Action received for U.S. Appl. No. 16/143,997, mailed on Sep. 30, 2019, 16 pages.
Final Office Action received for U.S. Appl. No. 16/144,030, mailed on Feb. 13, 2020, 11 pages.
Final Office Action received for U.S. Appl. No. 16/144,030, mailed on Oct. 1, 2019, 13 pages.
Final Office Action received for U.S. Appl. No. 16/144,735, mailed on May 4, 2020, 12 pages.
Final Office Action received for U.S. Appl. No. 16/144,753, mailed on Sep. 22, 2020, 9 pages.
Intention to Grant received for Danish Patent Application No. PA201870600, mailed on Jul. 10, 2019, 2 pages.
Intention to Grant received for Danish Patent Application No. PA201870601, mailed on Apr. 24, 2020, 2 pages.
Intention to Grant received for Danish Patent Application No. PA201870602, mailed on Apr. 24, 2020, 2 pages.
International Preliminary Report on Patentability received for PCT Patent Application No. PCT/US2018/031662, mailed on Nov. 28, 2019, 12 pages.
International Preliminary Report on Patentability received for PCT Patent Application No. PCT/US2019/019694, mailed on Sep. 24, 2020, 12 pages.
International Search Report and Written Opinion received for PCT Patent Application No. PCT/US2018/031662, mailed on Sep. 27, 2018, 17 pages.
International Search Report and Written Opinion received for PCT Patent Application No. PCT/US2019/019694, mailed on Sep. 2, 2019, 17 pages.
Invitation to Pay Addition Fees and Partial International Search Report received for PCT Patent Application No. PCT/US2018/031662, mailed on Jul. 16, 2018, 13 pages.
Invitation to Pay Additional Fees received for PCT Patent Application No. PCT/US2019/019694, mailed on Jul. 10, 2019, 12 pages.
Invitation to Pay Search Fees received for European Patent Application No. 19726205.8, mailed on Feb. 14, 2020, 5 pages.
Non-Final Office Action received for U.S. Appl. No. 15/705,849, mailed on Nov. 12, 2019, 15 pages.
Non-Final Office Action received for U.S. Appl. No. 16/143,909, mailed on Apr. 19, 2019, 16 pages.
Non-Final Office Action received for U.S. Appl. No. 16/143,959, mailed on Apr. 17, 2019, 15 pages.
Non-Final Office Action received for U.S. Appl. No. 16/143,997, mailed on Jul. 27, 2020, 15 pages.
Non-Final Office Action received for U.S. Appl. No. 16/143,997, mailed on May 21, 2019, 15 pages.
Non-Final Office Action received for U.S. Appl. No. 16/144,030, mailed on Apr. 12, 2019, 8 pages.
Non-Final Office Action received for U.S. Appl. No. 16/144,030, mailed on Nov. 5, 2020, 5 pages.
Non-Final Office Action received for U.S. Appl. No. 16/144,735, mailed on Feb. 19, 2020, 10 pages.
Non-Final Office Action received for U.S. Appl. No. 16/144,753, mailed on Mar. 5, 2020, 9 pages.
Notice of Acceptance received for Australian Patent Application No. 2018268972, mailed on Dec. 18, 2020, 3 pages.
Notice of Acceptance received for Australian Patent Application No. 2021200787, mailed on Mar. 19, 2021, 3 pages.
Notice of Allowance received for Chinese Patent Application No. 201910972529.2, mailed on Sep. 14, 2020, 6 pages (3 pages of English Translation and 3 pages of Official Copy).
Notice of Allowance received for Japanese Patent Application No. 2020-547369, mailed on Jul. 16, 2021, 4 pages (1 page of English Translation and 3 pages of Official Copy).
Notice of Allowance received for Korean Patent Application No. 10-2019-7033834, mailed on Jul. 3, 2021, 4 pages (2 page of English Translation and 2 pages of Official Copy).
Notice of Allowance received for Korean Patent Application No. 10-2020-7026391, mailed on May 11, 2021, 3 pages (1 page of Engiish Translation and 2 pages of Offcial Copy).
Notice of Allowance received for Korean Patent Application No. 10-2020-7026453, mailed on May 11, 2021, 3 pages (1 page of English Translation and 2 pages of Official Copy).
Notice of Allowance received for U.S. Appl. No. 15/705,849, mailed on Jul. 28, 2020, 10 pages.
Notice of Allowance received for U.S. Appl. No. 15/705,849, mailed on Oct. 16, 2020, 14 pages.
Notice of Allowance received for U.S. Appl. No. 16/143,909, mailed on Jan. 21, 2020, 9 pages.
Notice of Allowance received for U.S. Appl. No. 16/143,959, mailed on Oct. 31, 2019, 10 pages.
Notice of Allowance received for U.S. Appl. No. 16/143,997, mailed on May 13, 2021, 10 pages.
Notice of Allowance received for U.S. Appl. No. 16/144,030, mailed on Apr. 5, 2021, 8 pages.
Notice of Allowance received for U.S. Appl. No. 16/144,671, mailed on Feb. 10, 2020, 17 pages.
Notice of Allowance received for U.S. Appl. No. 16/144,735, mailed on Jul. 21, 2020, 13 pages.
Notice of Allowance received for U.S. Appl. No. 16/144,735, mailed on Oct. 28, 2020, 13 pages.
Notice of Allowance received for U.S. Appl. No. 16/144,753, mailed on Dec. 4, 2020, 22 pages.
Notice of Allowance received for U.S. Appl. No. 16/144,753, mailed on Feb. 10, 2021, 8 pages.
Office Action received for Australian Patent Application No. 2018268972, mailed on Jul. 9, 2020, 4 pages.
Office Action received for Australian Patent Application No. 2019100222, mailed on May 24, 2019, 6 pages.
Office Action received for Australian Patent Application No. 2019234289, mailed on Jul. 20, 2021, 4 pages.
Office Action received for Australian Patent Application No. 2019234289, mailed on Mar. 16, 2021, 8 pages.
Office Action received for Australian Patent Application No. 2019234289, mailed on Nov. 2, 2020, 6 pages.
Office Action received for Australian Patent Application No. 2020230340, mailed on Mar. 2, 2021, 6 pages.
Office Action received for Australian Patent Application No. 2020230340, mailed on May 27, 2021, 5 pages.
Office Action received for Australian Patent Application No. 2020230340, mailed on Nov. 2, 2020, 5 pages.
Office Action received for Chinese Patent Application No. 201910972529.2, mailed on Jun. 28, 2020, 8 pages (1 page of English Translation and 7 pages of Official Copy).
Office Action received for Chinese Patent Application No. 202010618240.3, mailed on Mar. 29, 2021, 21 pages (11 pages of English Translation and 10 pages of Official Copy).
Office Action received for Chinese Patent Application No. 202010618569.X, mailed on Mar. 12, 2021, 14 pages (7 pages of English Translation and 7 pages of Official Copy).
Office Action received for Chinese Patent Application No. 202011220489.5, mailed on Jun. 1, 2021, 12 pages (6 pages of English Translation and 6 pages of Official Copy).
Office Action received for Danish Patent Application No. PA201870599, mailed on Dec. 20, 2019, 5 pages.
Office Action received for Danish Patent Application No. PA201870600, mailed on May 8, 2019, 3 pages.
Office Action received for Danish Patent Application No. PA201870601, mailed on Dec. 13, 2018, 8 pages.

(56) References Cited

OTHER PUBLICATIONS

Office Action received for Danish Patent Application No. PA201870601, mailed on Jan. 14, 2020, 3 pages.
Office Action received for Danish Patent Application No. PA201870601, mailed on Jun. 25, 2019, 3 pages.
Office Action received for Danish Patent Application No. PA201870602, mailed on Feb. 5, 2020, 3 pages.
Office Action received for Danish Patent Application No. PA201870602, mailed on Jun. 26, 2019, 3 pages.
Office Action received for European Patent Application No. 18727543.3, mailed on Mar. 26, 2021, 7 pages.
Office Action received for European Patent Application No. 19726205.8, mailed on Jun. 26, 2020, 9 pages.
Office Action received for European Patent Application No. 20180581.9, mailed on Apr. 1, 2021, 11 pages.
Office Action received for European Patent Application No. 20180592.6, mailed on Apr. 1, 2021, 11 pages.
Office Action received for Japanese Patent Application No. 2019-563407, mailed on Feb. 5, 2021, 5 pages (2 pages of English Translation and 3 pages of Official Copy).
Office Action received for Japanese Patent Application No. 2020-153166, mailed on May 31, 2021, 6 pages (3 pages of English Translation and 3 pages of Official Copy).
Office Action received for Japanese Patent Application No. 2020-547369, mailed on Apr. 9, 2021, 4 pages (2 pages of English Translation and 2 pages of Official Copy).
Office Action received for Korean Patent Application No. 10-2019-7033834, mailed on Jan. 22, 2021, 13 pages (6 pages of English Translation and 7 pages of Official Copy).
Office Action received for Korean Patent Application No. 10-2020-7026391, mailed on Jan. 27, 2021, 5 pages (2 pages of English Translation and 3 pages of Official Copy).
Office Action received for Korean Patent Application No. 10-2020-7026453, mailed on Jan. 27, 2021, 5 pages (2 pages of English Translation and 3 pages of Official Copy).
Result of Consultation received for European Patent Application No. 19726205.8, mailed on Mar. 15, 2021, 19 pages.
Search Report and Opinion received for Danish Patent Application No. PA201870599, mailed on Dec. 21, 2018, 9 pages.
Search Report and Opinion received for Danish Patent Application No. PA201870600, mailed on Jan. 31, 2019, 8 pages.
Search Report and Opinion received for Danish Patent Application No. PA201870602, mailed on Dec. 19, 2018, 8 pages.
Search Report and Opinion received for Danish Patent Application No. PA202070395, mailed on Nov. 24, 2020, 10 pages.
Summons to Attend Oral Proceedings received for European Patent Application No. 19726205.8, mailed on Oct. 29, 2020, 13 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Corrected Notice of Allowance received for U.S. Appl. No. 16/143,997, mailed on Oct. 21, 2021, 2 pages.
Office Action received for Australian Patent Application No. 2020230340, mailed on Oct. 11, 2021, 4 pages.
Notice of Allowance received for Korean Patent Application No. 10-2022-7031866, mailed on May 1, 2023, 7 pages (2 pages of English Translation and 5 pages of Official Copy).
Office Action received for Australian Patent Application No. 2021261861, mailed on May 3, 2023, 4 pages.
Office Action received for Australian Patent Application No. 2022235614, mailed on May 9, 2023, 2 pages.
Notice of Allowance received for Chinese Patent Application No. 201880032190.1, mailed on Oct. 7, 2023, 4 pages (1 page of English Translation and 3 pages of Official Copy).
Notice of Allowance received for Japanese Patent Application No. 2023-110196, mailed on Feb. 13, 2024, 4 pages (1 page of English Translation and 3 pages of Official Copy).
Notice of Allowance received for U.S. Appl. No. 17/135,710, mailed on Feb. 14, 2024, 4 pages.
Alivecor Kardiab., "How to Record a Clean EKG With Kardiaband", Available Online at: https://www.youtube.com/watch?v=_Vlc9VE6VO4&t=2s, Nov. 30, 2017, 2 pages.
Extended European Search Report received for European Patent Application No. 23189089.8, mailed on Nov. 23, 2023, 11 pages.
Hardwick Tim, "AliveCor 'Kardia Band' Medical Grade EKG Analyzer for Apple Watch Receives FDA Approval", MacRumors, Available online at: https://www.macrumors.com/2017/11/30/alivecor-kardia-ekg-band-medical-fda-apple-watch/, Nov. 30, 2017, 3 pages.
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Office Action received for Japanese Patent Application No. 2023-028769, mailed on Apr. 1, 2024, 8 pages (4 pages of English Translation and 4 pages of Official Copy).
Applicant-Initiated Interview Summary received for U.S. Appl. No. 17/896,791, mailed on Oct. 12, 2023, 2 pages.
Office Action received for Australian Patent Application No. 2021261861, mailed on Sep. 22, 2023, 5 pages.
Corrected Notice of Allowance received for U.S. Appl. No. 17/896,791, mailed on Jan. 2, 2024, 2 pages.
International Search Report and Written Opinion received for PCT Patent Application No. PCT/US2023/022549, mailed on Aug. 1, 2023, 13 pages.
Notice of Allowance received for U.S. Appl. No. 17/896,791, mailed on Dec. 15, 2023, 9 pages.
Office Action received for Korean Patent Application No. 10-2021-7020689, mailed on May 14, 2024, 13 pages (6 pages of English Translation and 7 pages of Official Copy).
Notice of Allowance received for U.S. Appl. No. 17/135,710, mailed on Nov. 6, 2023, 7 pages.
Office Action received for Danish Patent Application No. PA202070395, mailed on Nov. 3, 2023, 3 pages.
Office Action received for Japanese Patent Application No. 2023-110196, mailed on Nov. 6, 2023, 4 pages (2 pages of English Translation and 2 pages of Official Copy).
Notice of Allowance received for U.S. Appl. No. 17/896,791, mailed on Mar. 13, 2024, 8 pages.
Office Action received for Korean Patent Application No. 10-2023-7025320, mailed on Mar. 11, 2024, 9 pages (4 pages of English Translation and 5 pages of Official Copy).
Notice of Allowance received for U.S. Appl. No. 17/135,710, mailed on Jan. 23, 2024, 7 pages.
Office Action received for Australian Patent Application No. 2023210876, mailed on Jun. 21, 2024, 2 pages.
Summons to Oral Proceedings received for European Patent Application No. 20180581.9, mailed on Jun. 25, 2024, 4 pages.
Corrected Notice of Allowance received for U.S. Appl. No. 17/896,791, mailed on Jun. 7, 2024, 2 pages.
Notice of Acceptance received for Australian Patent Application No. 2023210876, mailed on Aug. 20, 2024, 3 pages.
Result of Consultation received for European Patent Application No. 22190169.7, mailed on Sep. 4, 2024, 3 pages.
Communication for Board of Appeal received for European Patent Application No. 20180581.9, mailed on Jul. 8, 2024, 8 pages.
Notice of Allowance received for Korean Patent Application No. 10-2023-7025320, mailed on Jul. 31, 2024, 7 pages (2 pages of English Translation and 5 pages of Official Copy).
Office Action received for European Patent Application No. 22190169.7, mailed on Aug. 9, 2024, 10 pages.

* cited by examiner

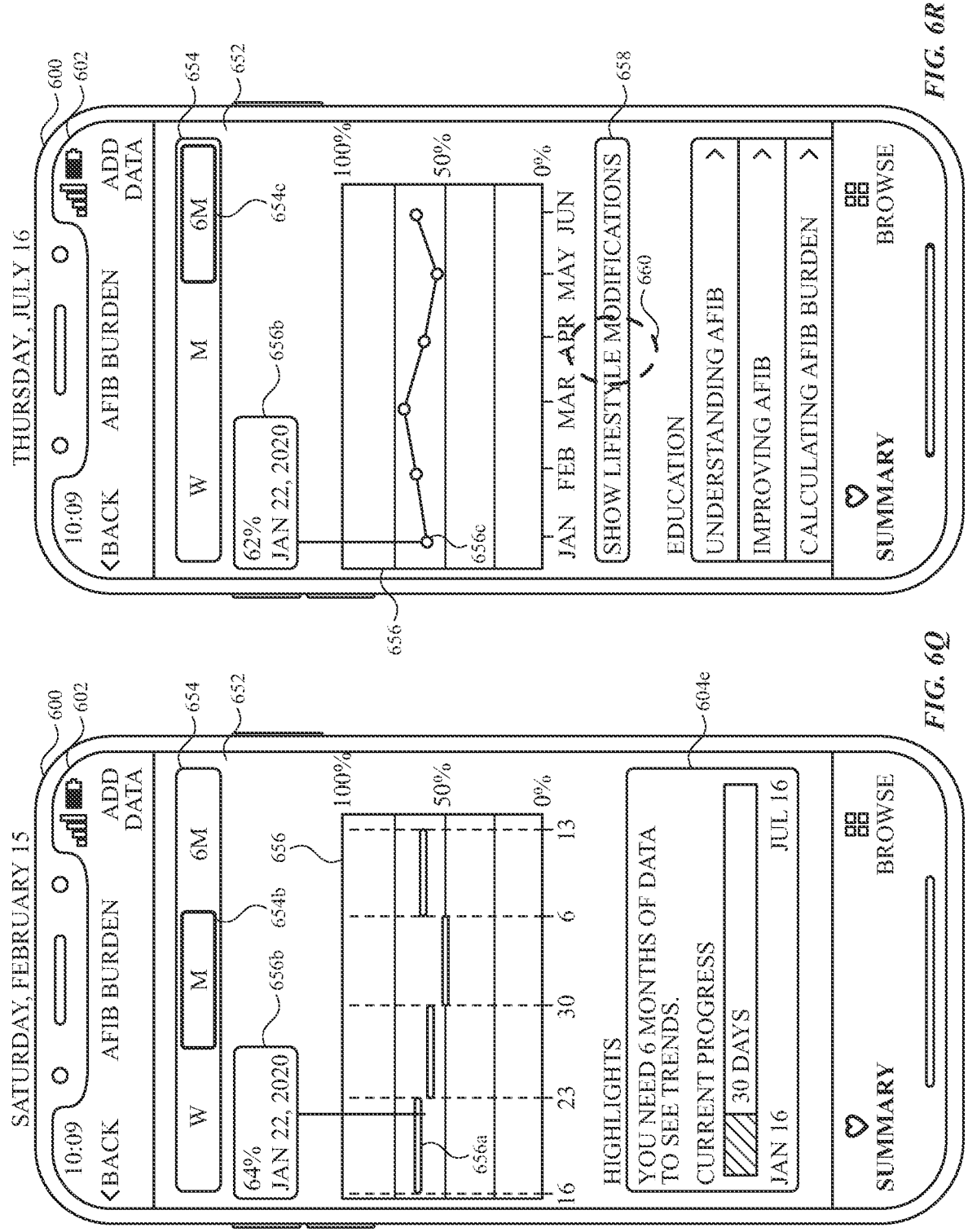

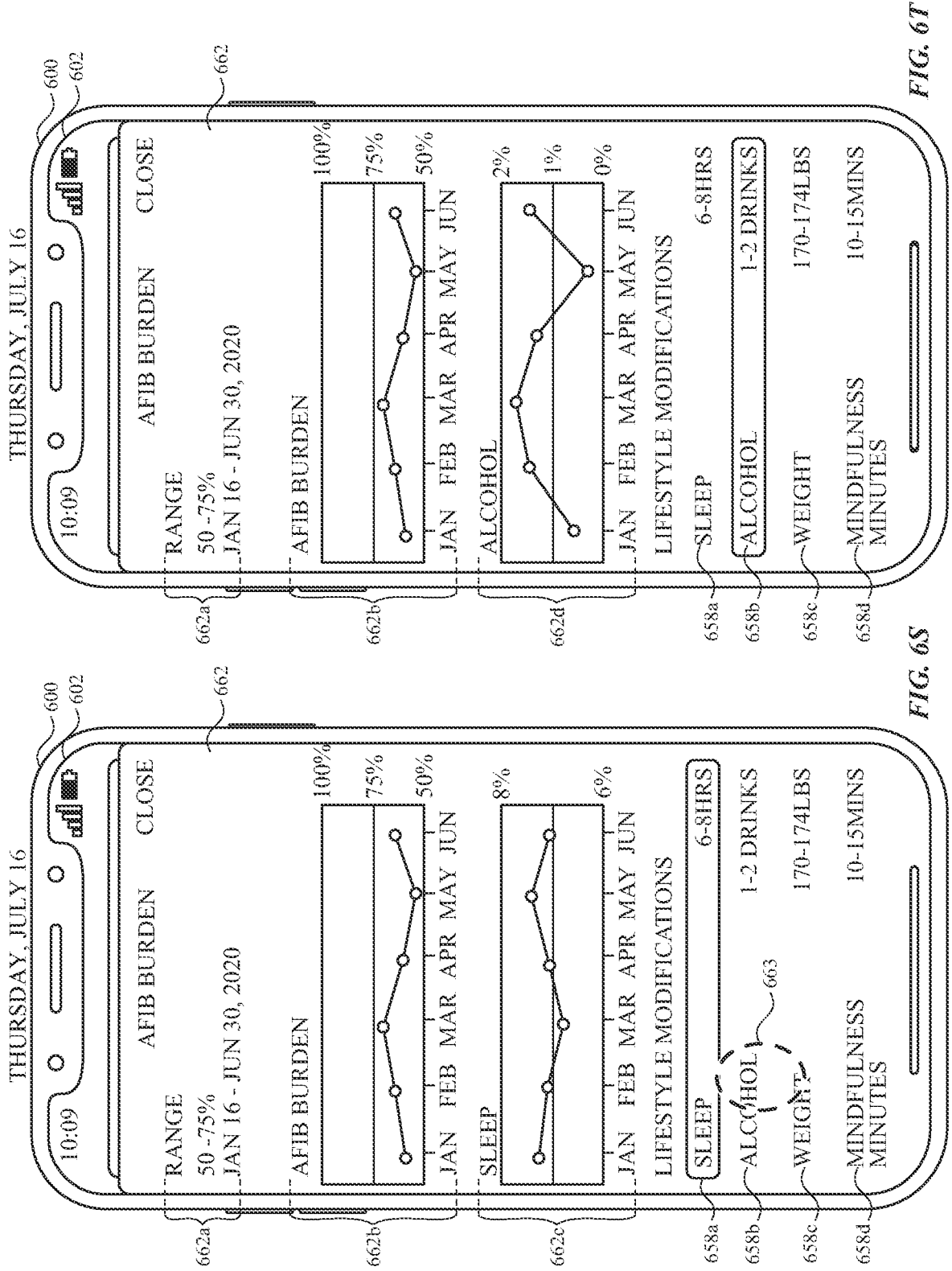

700 ⤸

702
Display, via the display generation component, a user interface that includes: a first representation of received atrial fibrillation data for a first time period; and a first representation of received non-heart data for the first time period.

704
Receiving data that corresponds to an atrial fibrillation event.

706
In accordance with a determination that a set of atrial fibrillation event notification criteria are met, output a notification indicating that an atrial fibrillation event has occurred.

708
In accordance with a determination that the set of atrial fibrillation event notification criteria are not met, forgo outputting the notification indicating that an atrial fibrillation event has occurred.

*FIG. 7*

ATRIAL FIBRILLATION USER INTERFACES

CROSS-REFERENCE TO RELATED APPLICATIONS

This application claims priority to U.S. Provisional Application No. 63/060,022, filed Aug. 1, 2020, entitled "ATRIAL FIBRILLATION USER INTERFACES," the entire contents of which are hereby incorporated by reference.

FIELD

The present disclosure relates generally to computer user interfaces, and more specifically to techniques for displaying atrial fibrillation data.

BACKGROUND

Computer systems can track, store, and present health data. Such systems can present health data from a number of sources.

BRIEF SUMMARY

Some techniques for presenting health data using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for displaying atrial fibrillation data. Such methods and interfaces optionally complement or replace other methods for displaying atrial fibrillation data. Such methods and interfaces reduce the cognitive burden on a user and produce a more efficient human-machine interface. For battery-operated computing devices, such methods and interfaces conserve power and increase the time between battery charges.

In accordance with some embodiments, a method, performed at a computer system that is in communication with a display generation component and one or more input devices is described. The method includes displaying, via the display generation component, a user interface that includes: a first representation of received atrial fibrillation data for a first time period; and a first representation of received non-heart data for the first time period.

In accordance with some embodiments, a non-transitory computer-readable storage medium storing one or more programs configured to be executed by one or more processors of computer system that is in communication with a display generation component and one or more input devices is described. The one or more programs include instructions for: displaying, via the display generation component, a user interface that includes: a first representation of received atrial fibrillation data for a first time period; and a first representation of received non-heart data for the first time period.

In accordance with some embodiments, a transitory computer-readable storage medium storing one or more programs configured to be executed by one or more processors of computer system that is in communication with a display generation component and one or more input devices is described. The one or more programs include instructions for: displaying, via the display generation component, a user interface that includes: a first representation of received atrial fibrillation data for a first time period; and a first representation of received non-heart data for the first time period.

In accordance with some embodiments, a computer system is described. The computer system includes: a display generation component; one or more input devices; one or more processors; and memory storing one or more programs configured to be executed by the one or more processors. The one or more programs include instructions for: displaying, via the display generation component, a user interface that includes: a first representation of received atrial fibrillation data for a first time period; and a first representation of received non-heart data for the first time period.

In accordance with some embodiments, a computer system including a display generation component and one or more input devices is described. The computer system also includes: means for displaying, via the display generation component, a user interface that includes: a first representation of received atrial fibrillation data for a first time period; and a first representation of received non-heart data for the first time period.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying atrial fibrillation data, thereby increasing the effectiveness, efficiency, and user satisfaction with such devices. Such methods and interfaces may complement or replace other methods for displaying atrial fibrillation data.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 7 is a flow diagram illustrating a method for displaying atrial fibrillation data, in accordance with some embodiments.

DESCRIPTION OF EMBODIMENTS

Figure 1A:
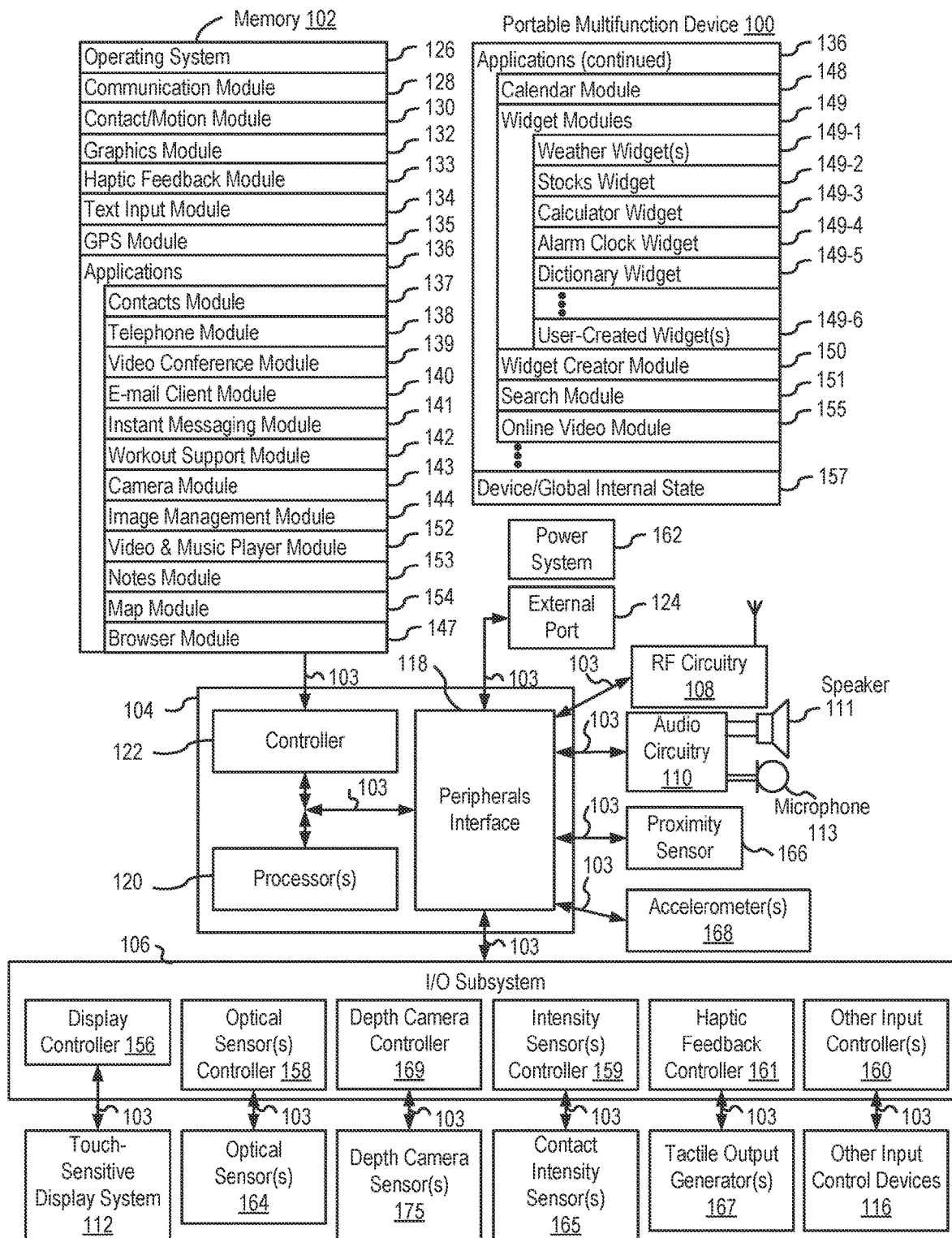
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying atrial fibrillation data. Further, electronic devices should provide displays of atrial fibrillation data along with other user behavior data in order for a user to determine relationships between user behavior and atrial fibrillation. These techniques can reduce the cognitive burden on a user who accesses atrial fibrillation data and tries to determine ways to reduce time he or she has an irregular heartbeat, thereby enhancing productivity. Further, such techniques can reduce processor and battery power otherwise wasted on redundant user inputs.

Below, FIGS. 1A-1B, 2, 3, 4A-4B, and 5A-5B provide a description of exemplary devices for performing the techniques for managing event notifications. FIGS. 6A-6Y illustrate exemplary user interfaces for displaying atrial fibrillation data. FIG. 7 is a flow diagram illustrating methods for displaying atrial fibrillation data in accordance with some embodiments. The user interfaces in FIGS. 6A-6Y are used to illustrate the processes described below, including the processes in FIG. 7.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VOIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
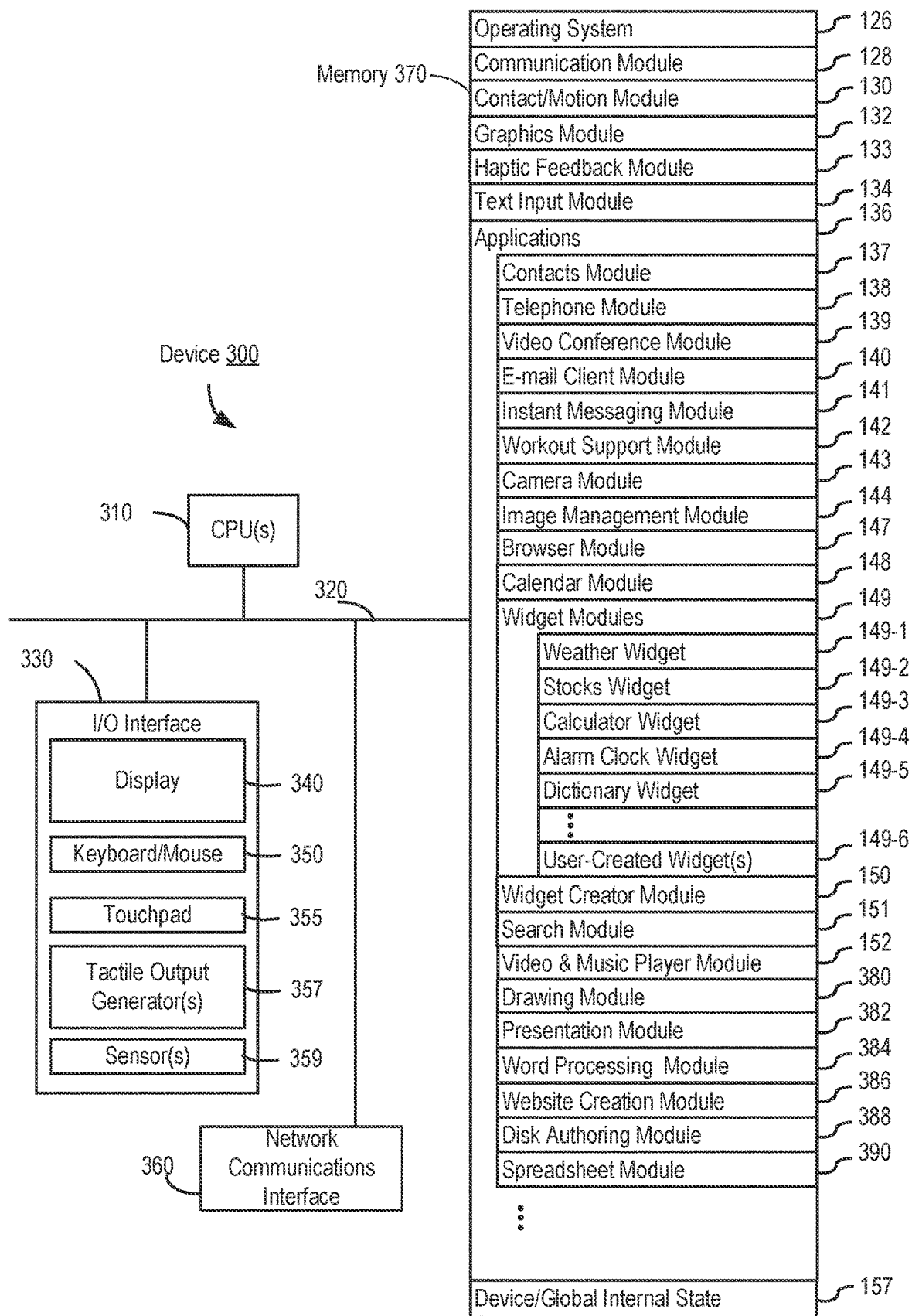
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, IOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
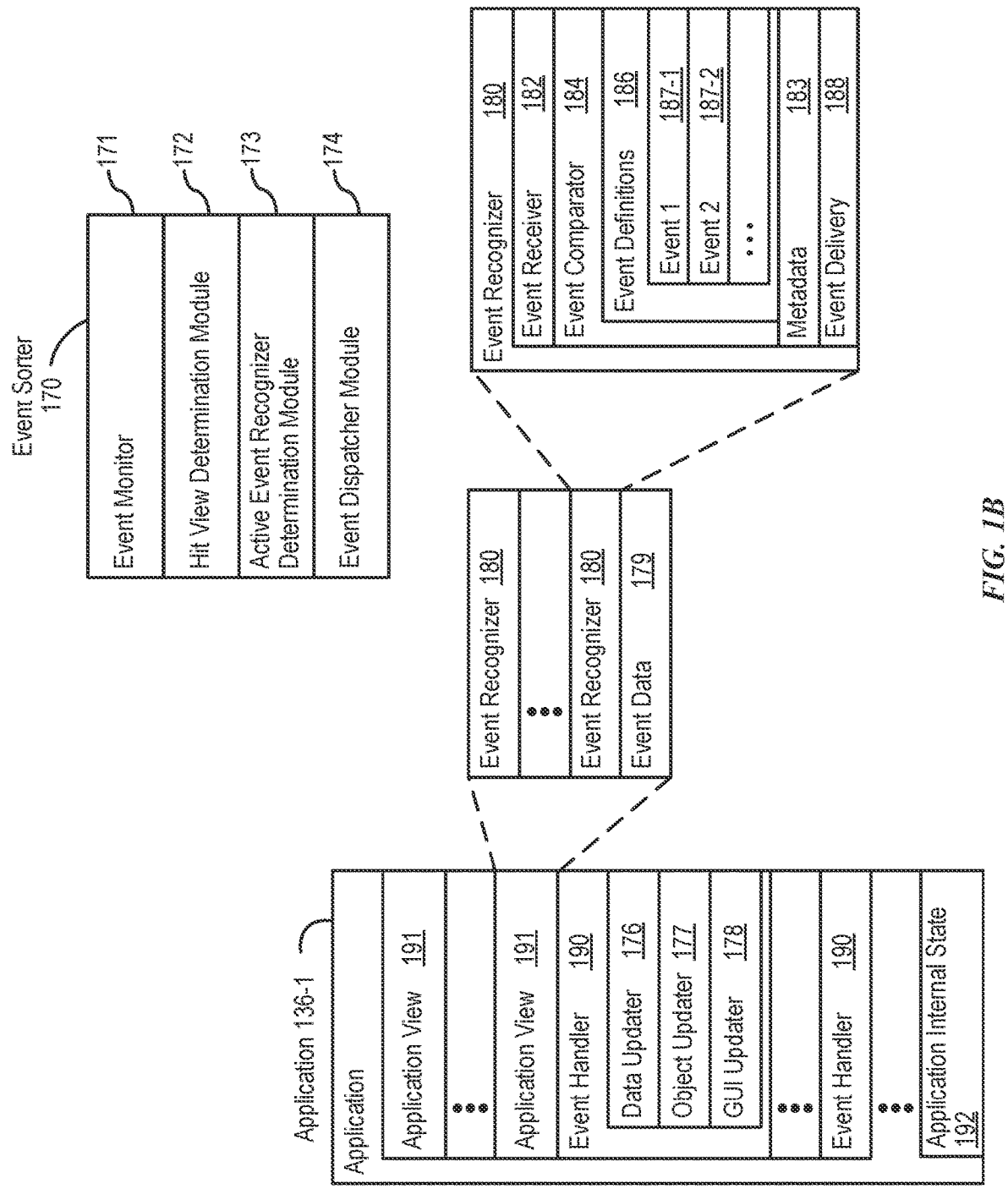
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
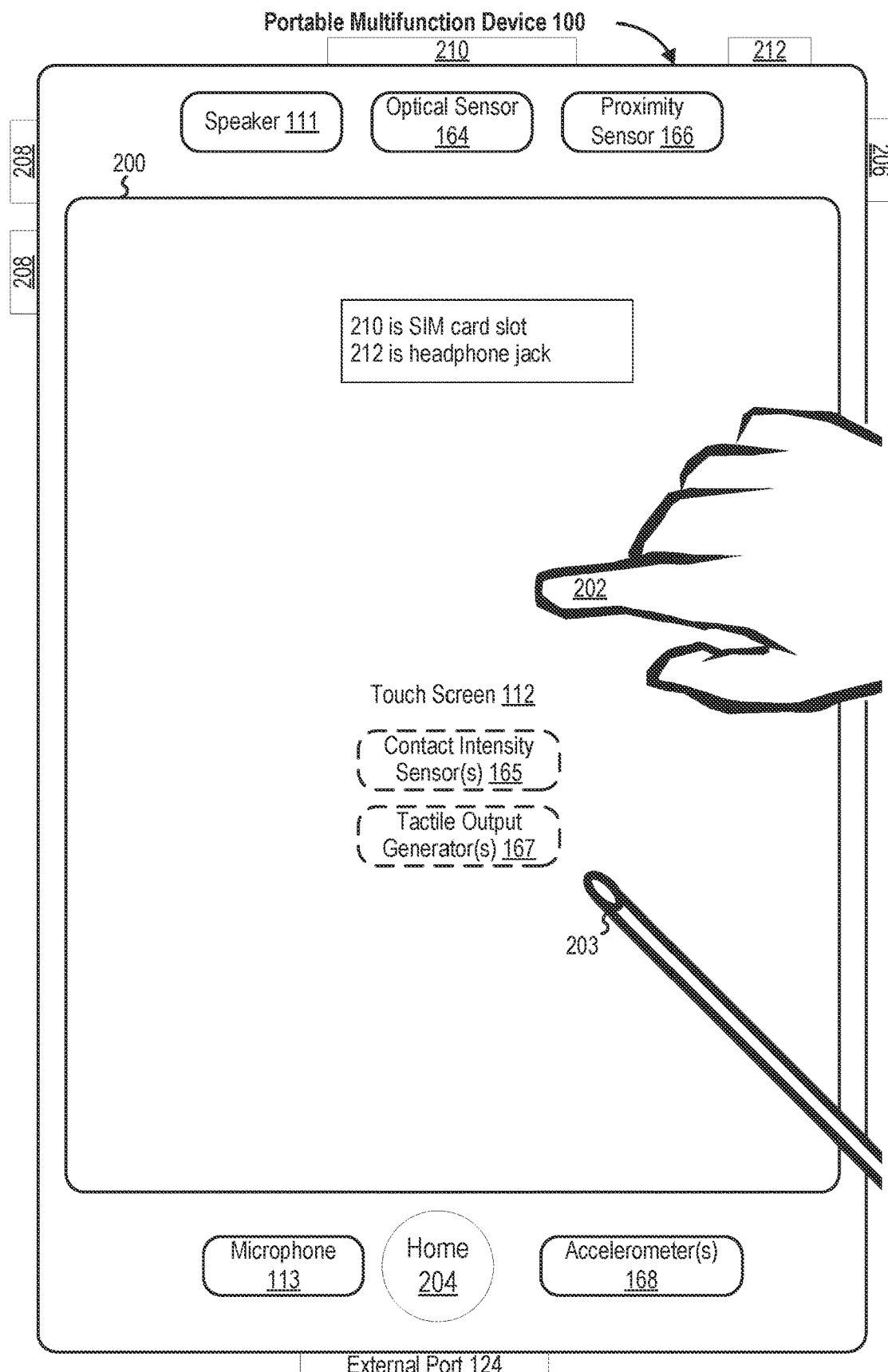
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
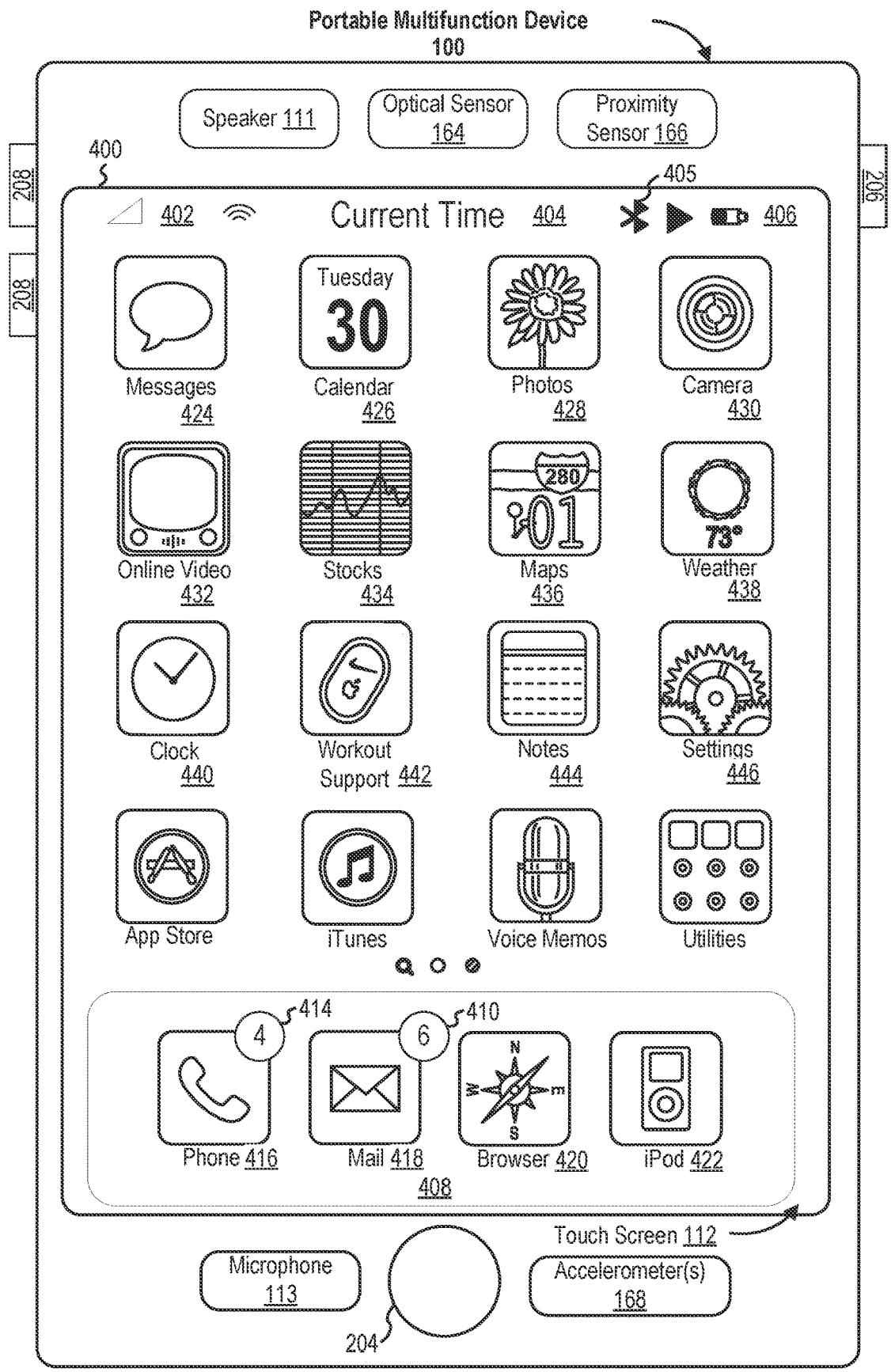
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
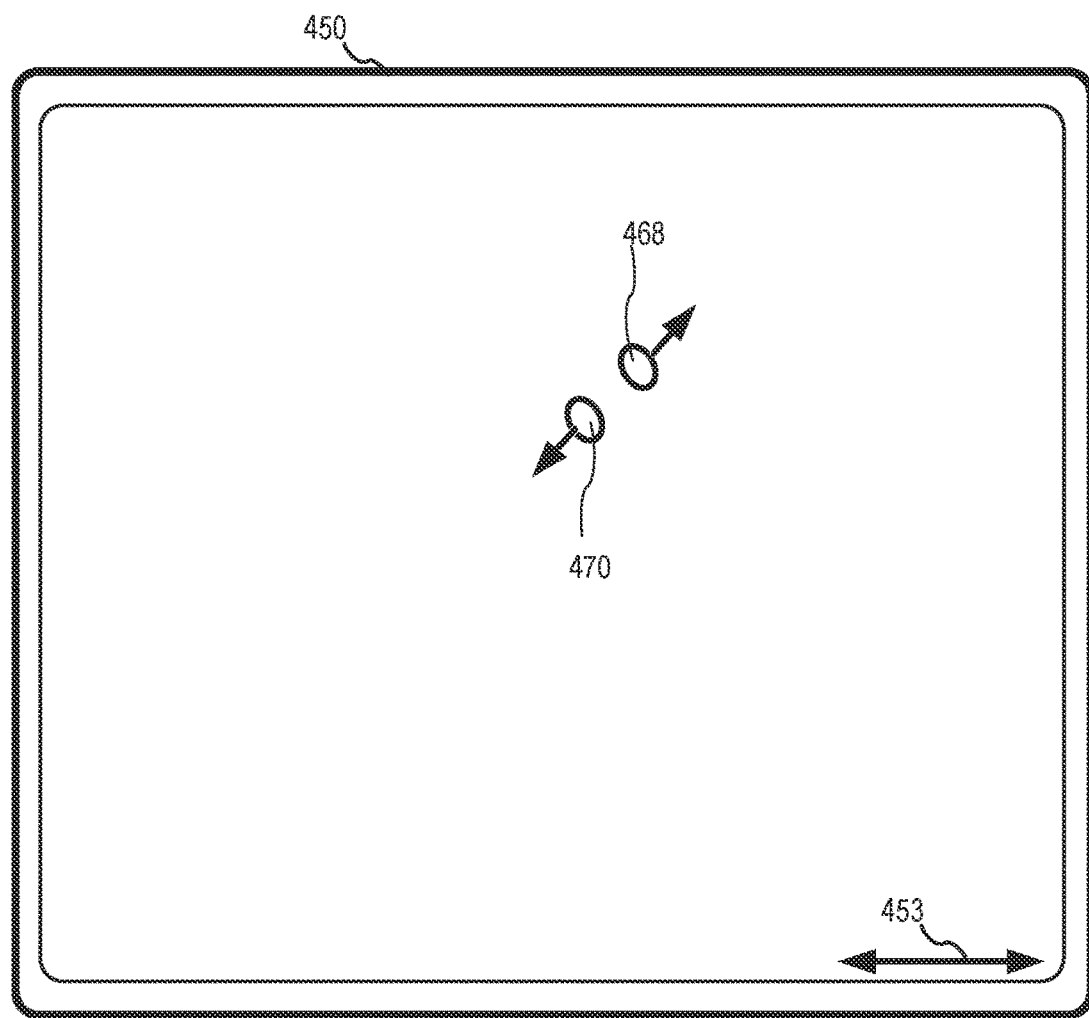
FIG. 4B illustrates an exemplary user interface for a multifunction device with a touch-sensitive surface that is separate from the display in accordance with some embodiments.
Figure 4B:
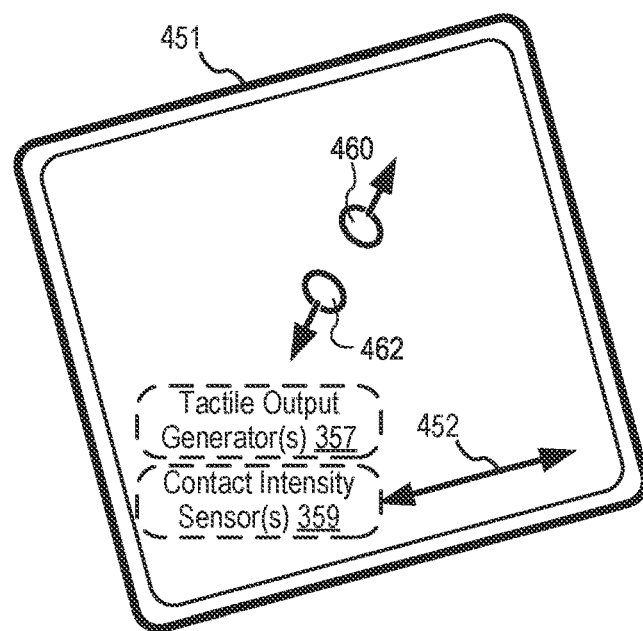

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
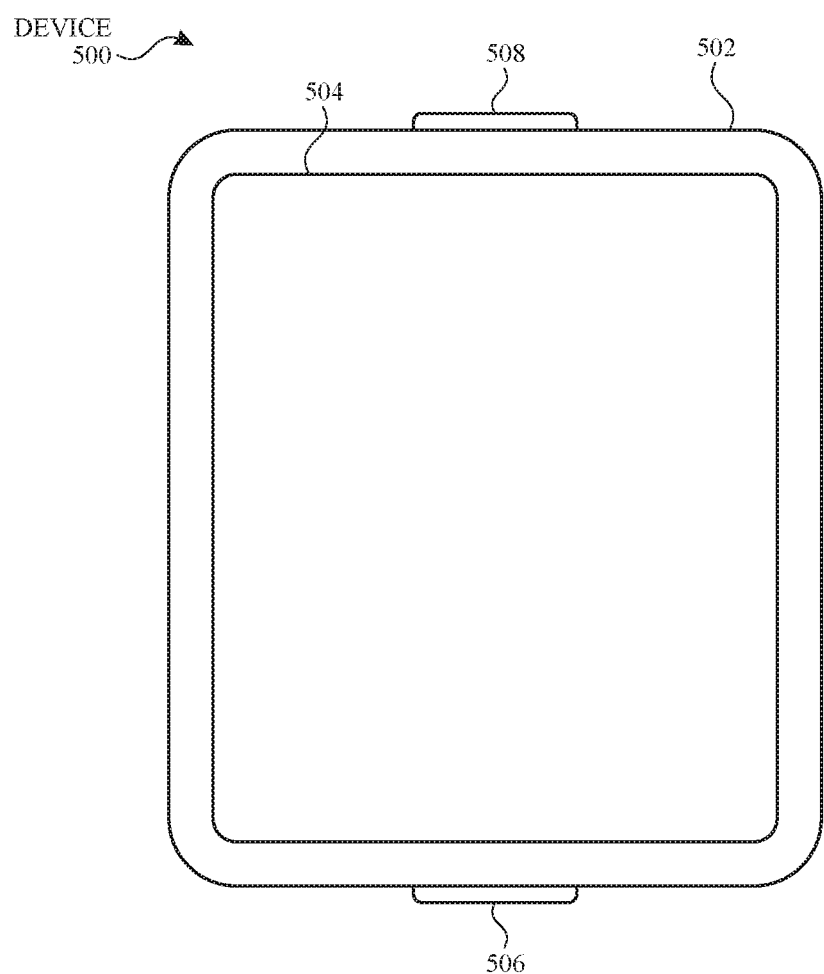
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
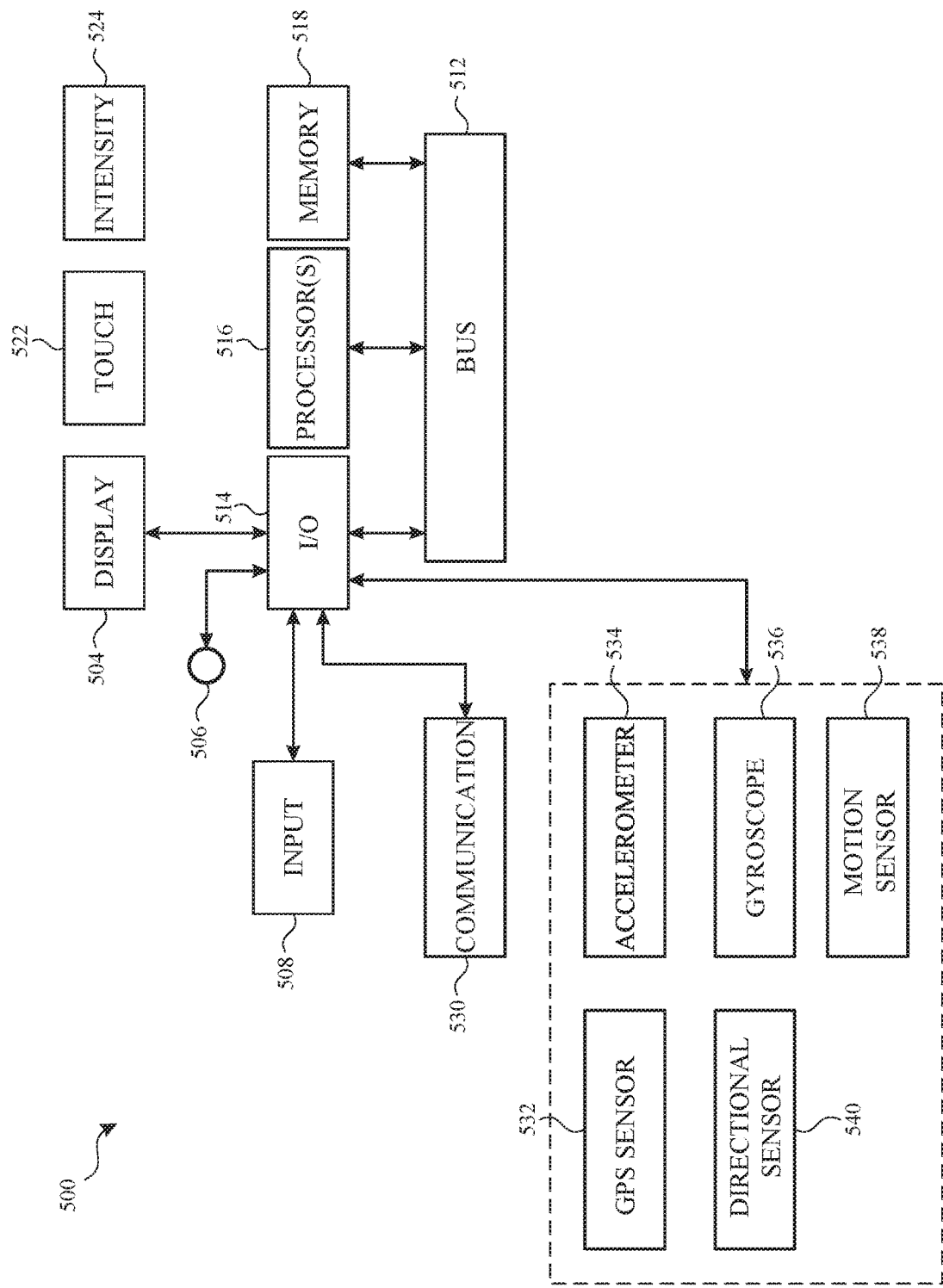
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including process 700 (FIG. 7). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6Y illustrate exemplary user interfaces for displaying atrial fibrillation data, in accordance with some embodiments. The user interfaces in these figures are used to illustrate the processes described below, including the processes in FIG. 7.

FIG. 6A illustrates electronic device 600 displaying health application user interface 604 on touchscreen display 602. In some embodiments, device 600 includes one or more features of devices 100, 300, and/or 500. The current date is THURSDAY, January 16, as indicated above device 600. Health application user interface 604 includes atrial fibrillation burden setup prompt 604a, which reads "YOUR WATCH CAN MEASURE ATRIAL FIBRILLATION BURDEN," and set up affordance 604b. In some embodiments, atrial fibrillation data is collected using biometric sensors on an external device (e.g., a smart watch, a heart monitor) that is in communication with electronic device 600. In some embodiments, the external device 668 depicted in FIGS. 6W-6Y, as discussed in more detail, below. Device 600 detects tap input 606 corresponding to selection of set up affordance 604b. In the embodiment of FIGS. 6A-6Y, atrial fibrillation burden refers to the proportion of time that a subject (e.g., the user of device 600) is in atrial fibrillation during a given time period.

Figure 6B:
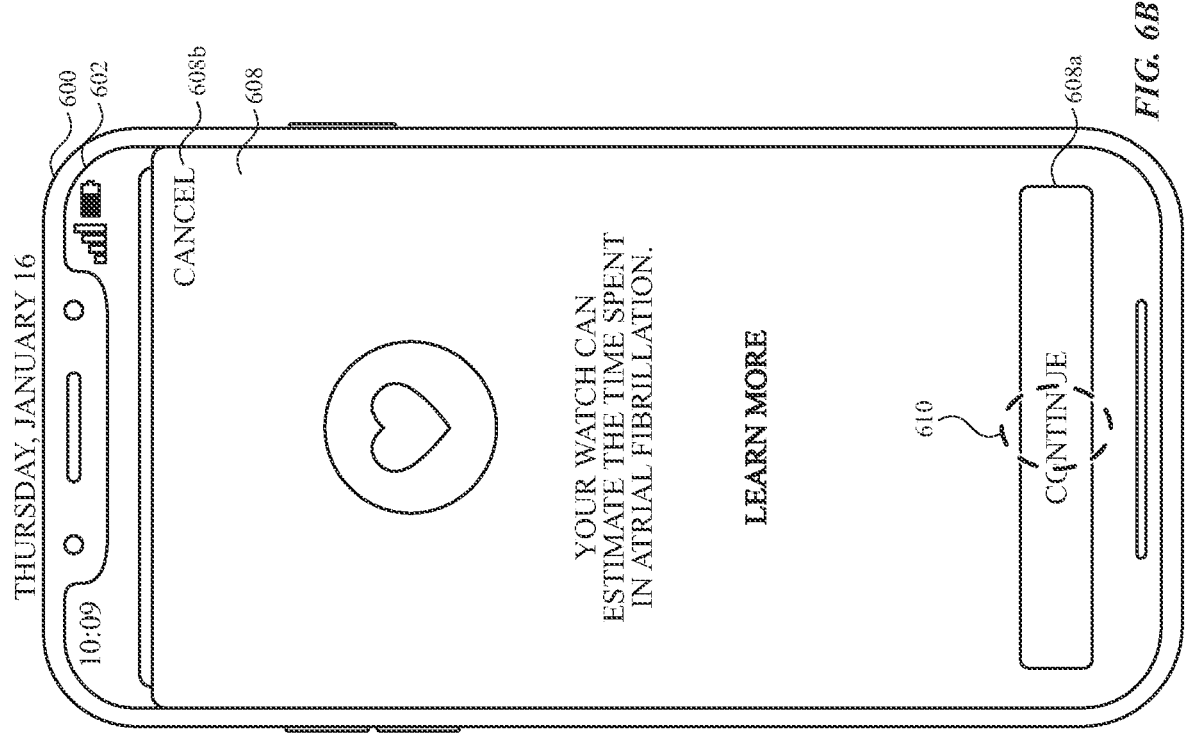
FIGS. 6A-6Y illustrate exemplary user interfaces for displaying atrial fibrillation data, in accordance with some embodiments.
Figure 6A:
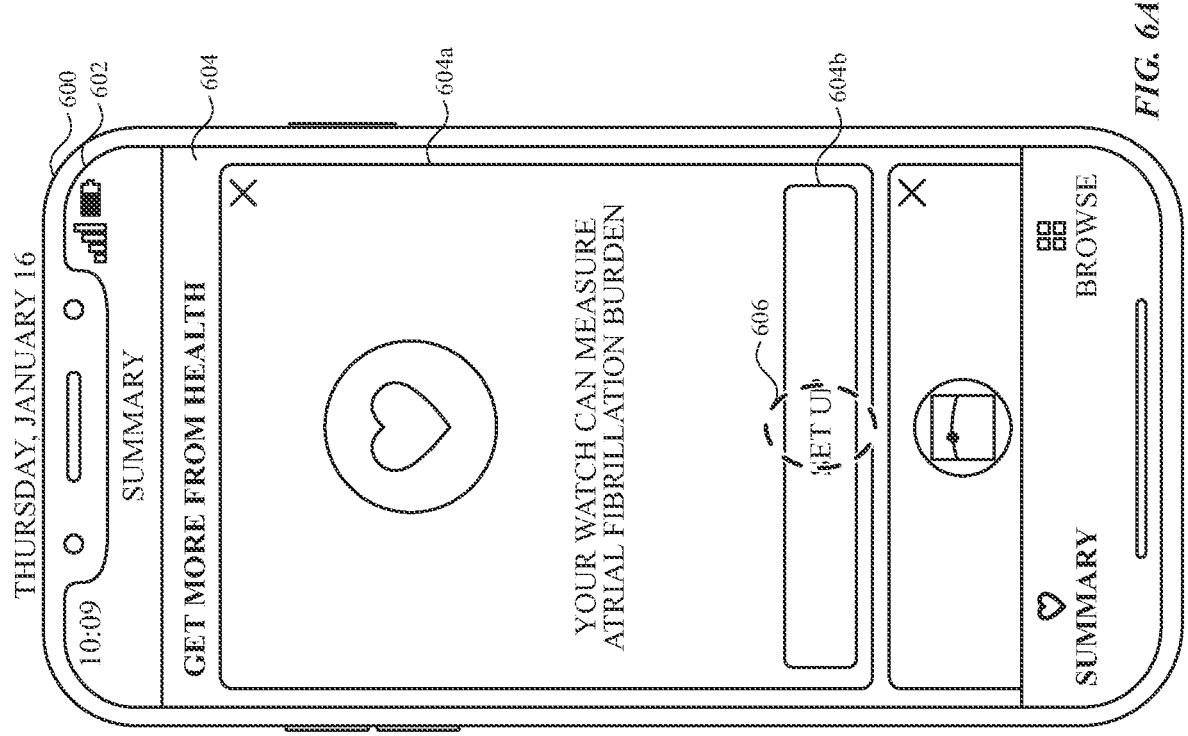
Figures 6C, 6D:
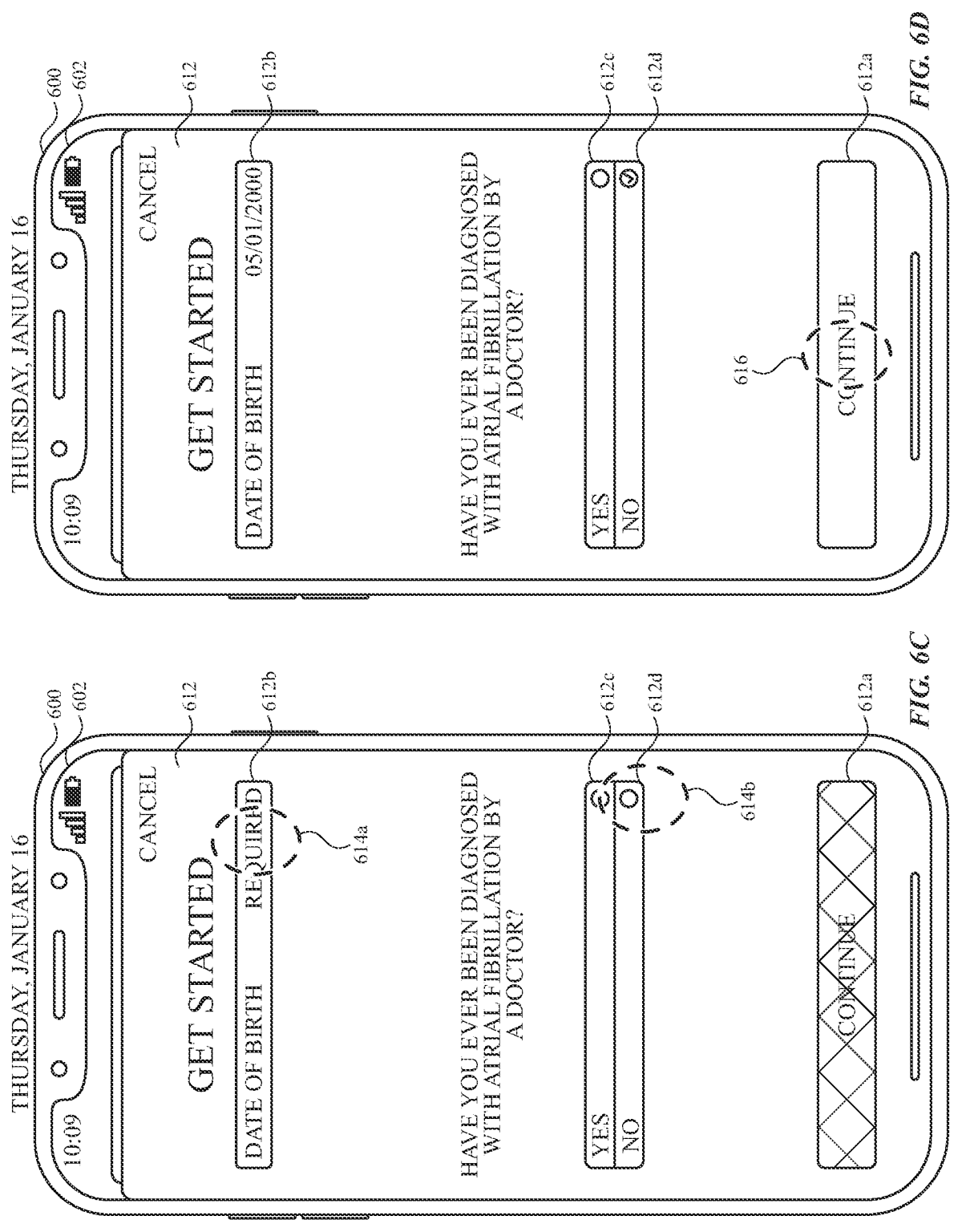
Figure 6F:
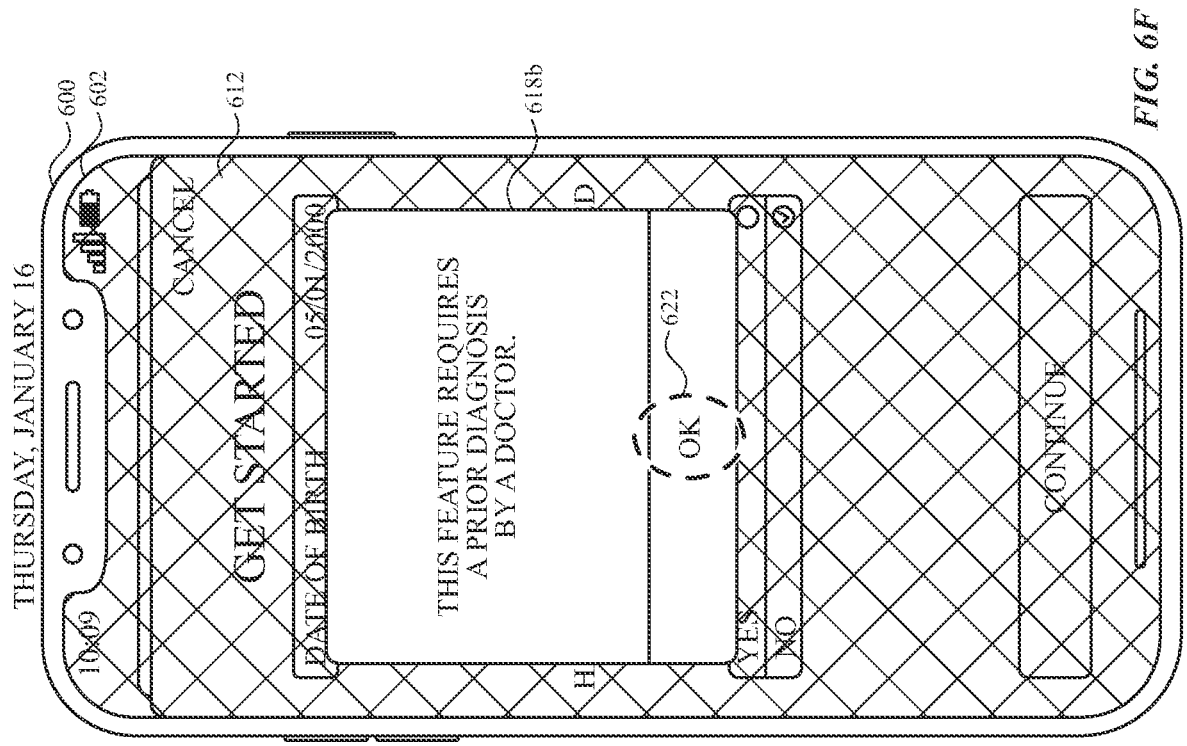

In response to receiving tap input 606 at set up affordance 604b, device 600 initiates onboarding for atrial fibrillation burden tracking and displays onboarding user interface 608 on touchscreen display 602, as shown in FIG. 6B. Onboarding user interface 608 includes information about the atrial fibrillation burden tracking feature and text "LEARN MORE." In some embodiments, device 600 detects a tap input on text "LEARN MORE" and displays additional information about atrial fibrillation. In some embodiments, multiple informational user interfaces will be displayed sequentially during onboarding. Onboarding user interface 608 includes continue affordance 608a and cancel affordance 608b. When activated by tap input, cancel affordance 608b causes device 600 to exit onboarding for atrial fibrillation burden tracking and returns to displaying health application user interface 604 of FIG. 6A. Device 600 detects tap input 610 corresponding to selection of continue affordance 608a to proceed with onboarding for atrial fibrillation burden tracking and displays information collection user interface 612, as shown in FIG. 6C.

FIG. 6C depicts device 600 displaying information collection user interface 612 on touchscreen display 602. Information collection user interface 612 includes continue affordance 612a having hatching to indicate that the continue affordance is in a disabled state. In some embodiments, continue affordance 612a is grayed out. In some embodiments, device 600 does not respond to detection of a touch input at continue affordance 612a while the continue affordance is in the disabled state.

Information collection user interface 612 further includes date of birth field 612b and diagnosis affordances 612c and 612d, corresponding to selection of "YES" and "NO," respectively, in response to the prompt, "HAVE YOU EVER BEEN DIAGNOSED WITH ATRIAL FIBRILLATION BY A DOCTOR?" Device 600 detects tap input 614a corresponding to selection of date of birth field 612b. In some embodiments, in response to detecting tap input 614a, device 600 displays a keyboard, numeric keypad, or date selection mechanism for the user to enter their birthdate. Device 600 also detects tap input 614b corresponding to selection of diagnosis field 612d corresponding to selection of "NO," indicating that the user has not been diagnosed with atrial fibrillation by a doctor. In response to detecting tap input 614b, device 600 displays a check mark in diagnosis field 612d corresponding to "NO," as shown in FIG. 6D.

As shown in FIG. 6D, once the date of birth field 612b has been filled in, as shown by "05/01/2000," and diagnosis affordance 612d has been selected, device 600 displays continue affordance 612a without hatching to indicate that the continue affordance is now in an active state. Once date of birth field 612b has been populated, selection of diagnosis affordance 612c corresponding to "YES" also causes device 600 to display continue affordance 612a without hatching and in the active state, as shown in FIG. 6G. Device 600 detects tap input 616 corresponding to selection of continue affordance 612a.

Figure 6E:
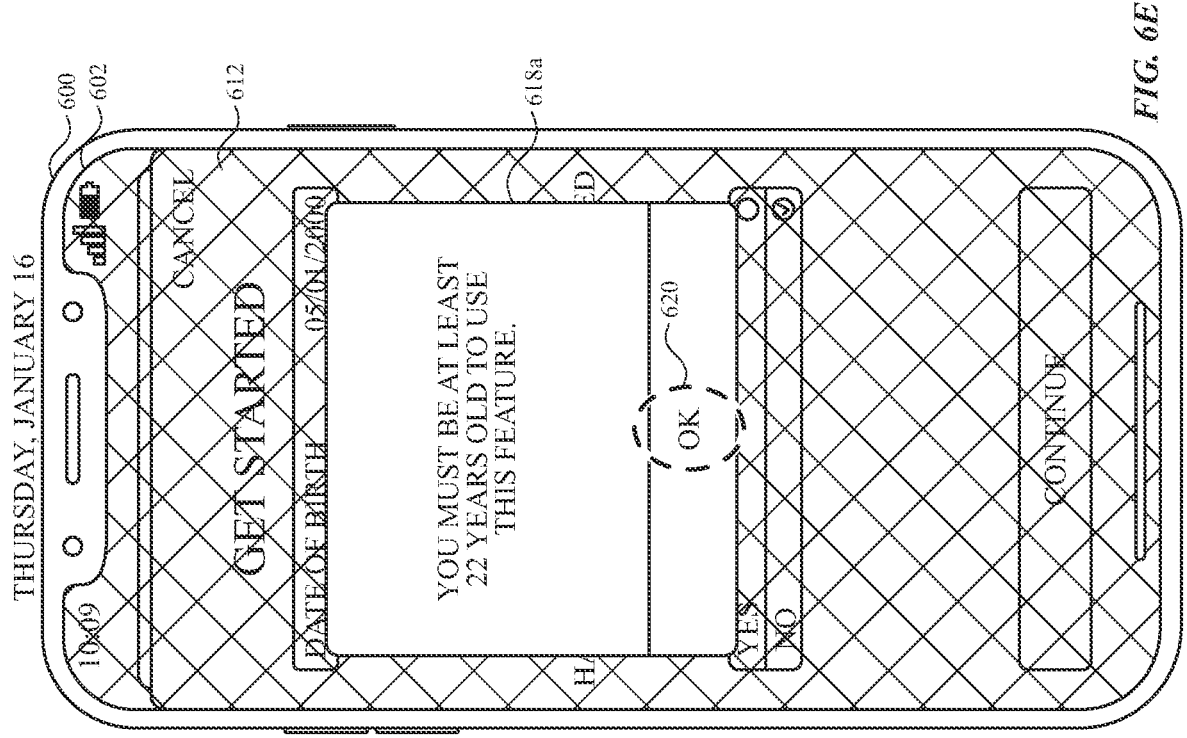

As shown in FIG. 6E, in response to detecting tap input 616, device 600 displays, on touchscreen display 602, minimum age notification 618a overlaid on information collection user interface 612. Information collection user interface 612 is deemphasized on touchscreen display 602, as indicated by the hatching. In some embodiments, deemphasizing information collection user interface 612 includes a blur treatment and/or dimming a portion of the display. Minimum age notification 618a reads, "YOU MUST BE AT LEAST 22 YEARS OLD TO USE THIS FEATURE" and is displayed when the birthdate entered in date of birth field 612b is less than 22 years prior to the current date. In some embodiments, the minimum age is another age, such as 18. In some embodiments, the atrial fibrillation burden tracking feature does not have a minimum age requirement. Device 600 detects tap input 620 on "OK" of minimum age notification 618a. In some embodiments, tapping "OK" causes device 600 to dismiss minimum age notification 618a and display information collection user interface 612 of FIG. 6D. In some embodiments, tapping "OK" causes device 600 to exit onboarding and return to displaying health application user interface 604 of FIG. 6A. Device 600 foregoes display of minimum age notification 618a if the birthdate entered in date of birth field 612b is more than 22 years prior to the current date, as discussed with respect to FIG. 6G below.

Similar to FIG. 6E, in FIG. 6F, device 600 displays diagnosis requirement notification 618b overlaid on information collection user interface 612 in response to detecting tap input 616. Diagnosis requirement notification 618b reads, "THIS FEATURE REQUIRES A PRIOR DIAGNOSIS BY A DOCTOR" and is displayed when diagnosis affordance 612d corresponding to "NO" is selected, indicating that the user has not been diagnosed with atrial fibrillation by a doctor. Device 600 detects tap input 622 on "OK" of diagnosis requirement notification 618b. In some embodiments, tapping "OK" causes device 600 to diagnosis requirement notification 618b and display information collection user interface 612 of FIG. 6D. In some embodiments, tapping "OK" causes device 600 to exit onboarding and return to displaying health application user interface 604 of FIG. 6A. Device 600 foregoes display of diagnosis requirement notification 618b if diagnosis affordance 612c corresponding to "YES" is selected, as discussed with respect to FIG. 6G.

Turning now to FIG. 6G, device 600 displays information collection user interface 612 having date of birth field 612b filled in with a birthdate more than 22 years prior to the current date and diagnosis affordance 612c corresponding to "YES" selected, indicating that the user has been diagnosed with atrial fibrillation by a doctor. In some embodiments, additional verification that the user was diagnosed with atrial fibrillation by a doctor is required. Device 600 displays continue affordance 612a in an active state. Device 600 detects tap input 624 corresponding to selection of continue affordance 612a, which causes device 600 to display activation notification 626, as shown in FIG. 6H.

Figure 6H:
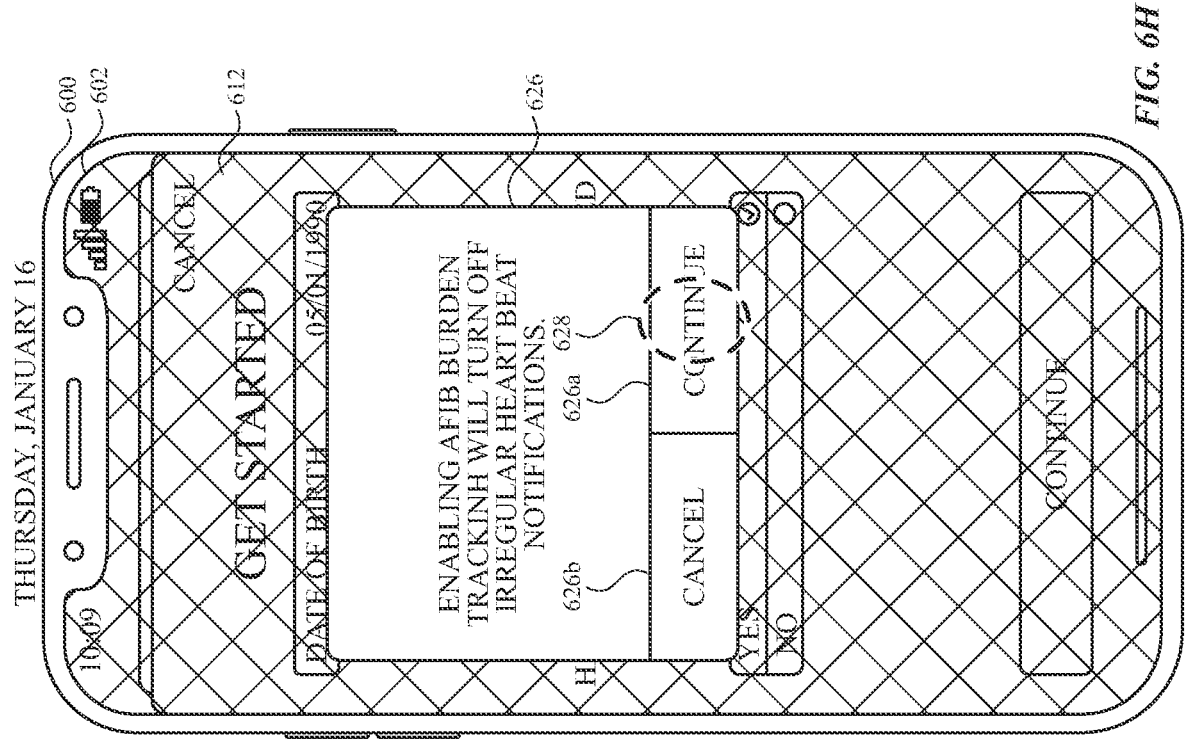
Figure 6G:
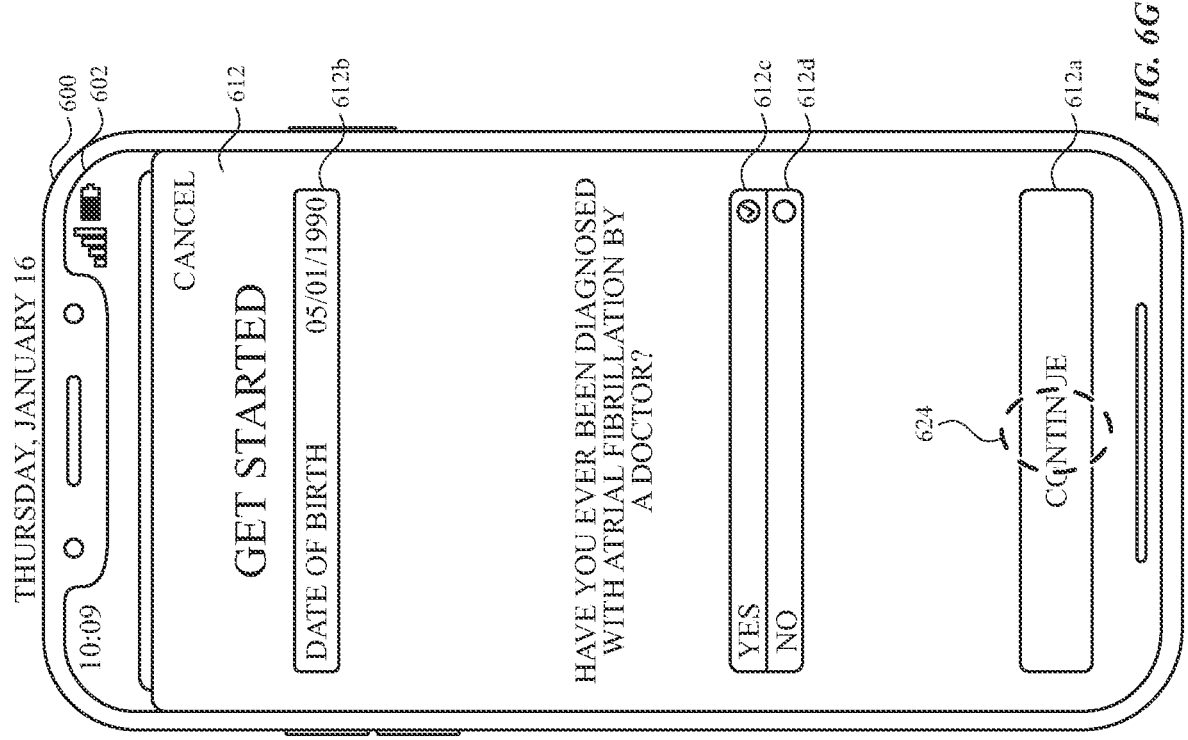

In FIG. 6H, device 600 displays, on touchscreen display 602, activation notification 626 overlaid on information collection user interface 612. Similar to FIG. 6E, information collection user interface 612 is deemphasized on touchscreen display 602, as indicated by the hatching. Activation notification 626 reads, "ENABLING ATRIAL FIBRILLATION BURDEN TRACKING WILL TURN OFF IRREGULAR HEARTBEAT NOTIFICATIONS" to notify the user that device 600 will deactivate notifications for discrete atrial fibrillation events. Additional details regarding atrial fibrillation event notifications can be found in U.S. patent application Ser. No. 16/144,030 titled "USER INTERFACES FOR HEALTH MONITORING", filed Sep. 27, 2018, which is hereby incorporated by reference in its entirety for all purposes and especially for its disclosure of atrial fibrillation event notifications. In some embodiments, device 600 displays activation notification 626 if notifications for discrete atrial fibrillation events are enabled at the time of atrial fibrillation burden tracking onboarding. In some embodiments, device 600 forgoes display of activation notification 626 if notifications for discrete atrial fibrillation events are not enabled at the time of atrial fibrillation burden tracking onboarding. In some embodiments, notifications for discrete atrial fibrillation events are enabled when the atrial fibrillation burden tracking is disabled. Activation notification 626 further includes continue affordance 626a and cancel affordance 626b. In some embodiments, activation of cancel affordance 626b by a tap input causes device 600 to exit onboarding for atrial fibrillation burden tracking and returns to displaying health application user interface 604 of FIG. 6A. In some embodiments, activation of cancel affordance 626b by a tap input causes device 600 to dismiss activation notification 626 and display information collection user interface 612 as shown in FIG. 6G. As shown in FIG. 6H, device 600 detects tap input 628 corresponding to selection of continue affordance 626a and proceeds with onboarding for atrial fibrillation burden tracking.

As shown in 6I, in response to detecting tap input 628 in FIG. 6H, device 600 displays measurement information user interface 630. Measurement information user interface 630 details that atrial fibrillation burden is the percentage of data samples collected by the sensors that were in atrial fibrillation for a particular time period. Measurement information user interface 630 teaches the user that lower atrial fibrillation burden percentages correlate with less frequent detection of atrial fibrillation events during a particular time period and higher atrial fibrillation burden percentages correlate with more frequent detection of atrial fibrillation events during a particular time period. In some embodiments, multiple informational user interfaces are displayed during onboarding for atrial fibrillation burden tracking. Device 600 detects tap input 632 corresponding to selection of continue affordance 630a and displays lifestyle modification user interface 634 in FIG. 6J.

Figure 6J:
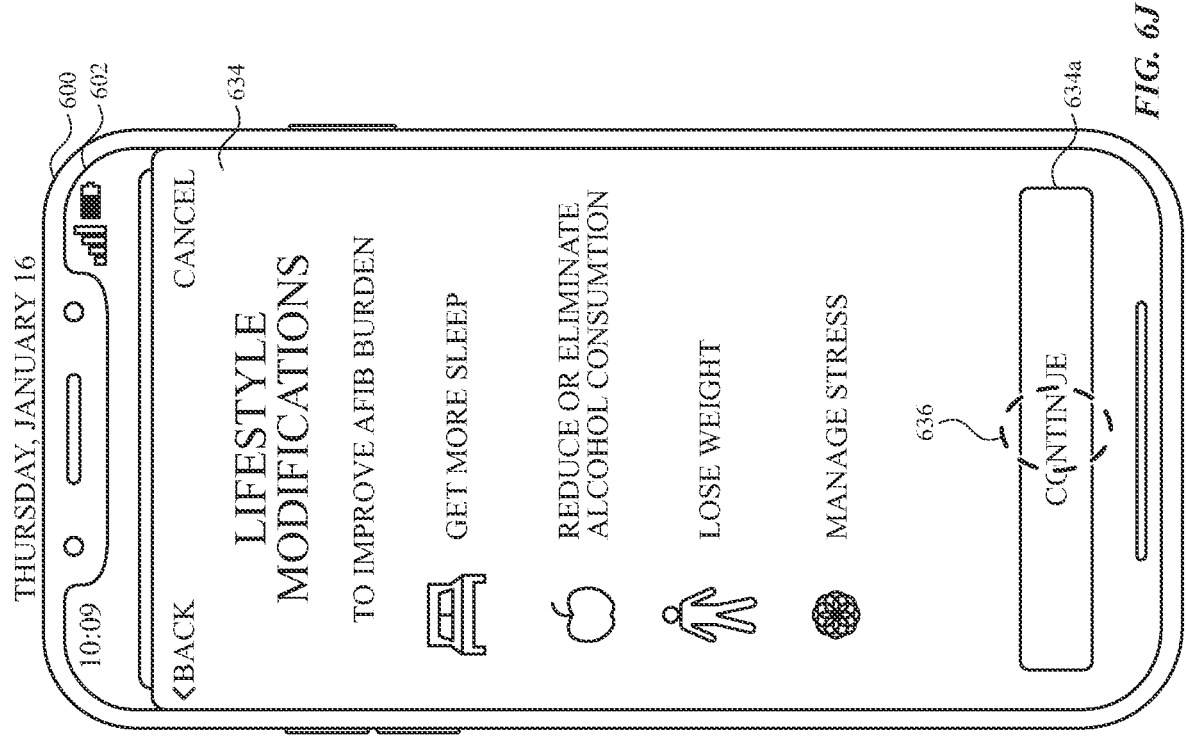
Figure 6I:
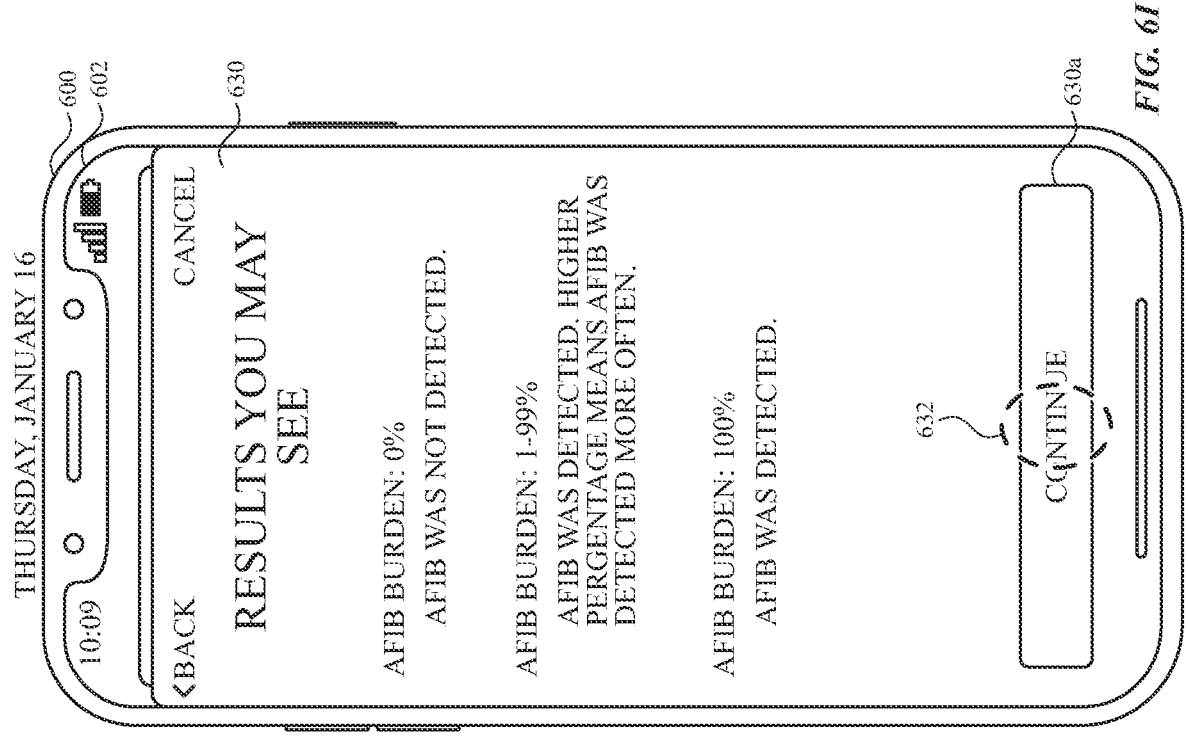

In FIG. 6J, device 600 displays lifestyle modification user interface 634 on touchscreen display 602. Lifestyle modification user interface 634 includes suggestions for actions (e.g., actions that can be tracked, entered, and/or recorded) that can be taken to potentially improve (e.g., reduce) atrial fibrillation burden. The displayed lifestyle modification factors include getting more sleep, reducing alcohol consumption, losing weight, and managing stress. In some embodiments, reducing caffeine intake is also listed on lifestyle modification user interface 634. One of ordinary skill in the art can contemplate additional or alternative lifestyle modifications, e.g., changes to a user's behavior or habits, that can reduce the time a user experiences atrial fibrillation. In some embodiments, a subset of suggested lifestyle modifications are shown on lifestyle modification user interface 634. In some embodiments, lifestyle modification user interface 634 includes additional details related to each lifestyle modification. Device 600 detects tap input 636 corresponding to selection of continue affordance 634a and proceeds with onboarding for atrial fibrillation burden tracking.

Figure 6L:
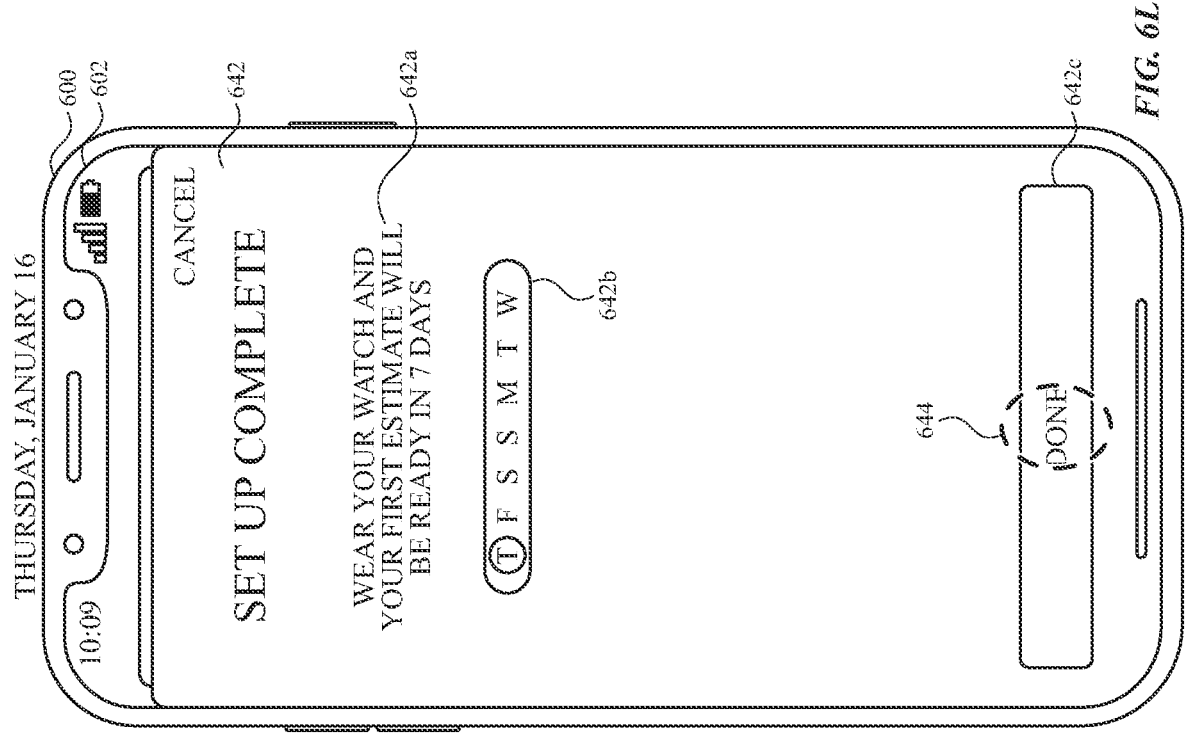
Figure 6K:
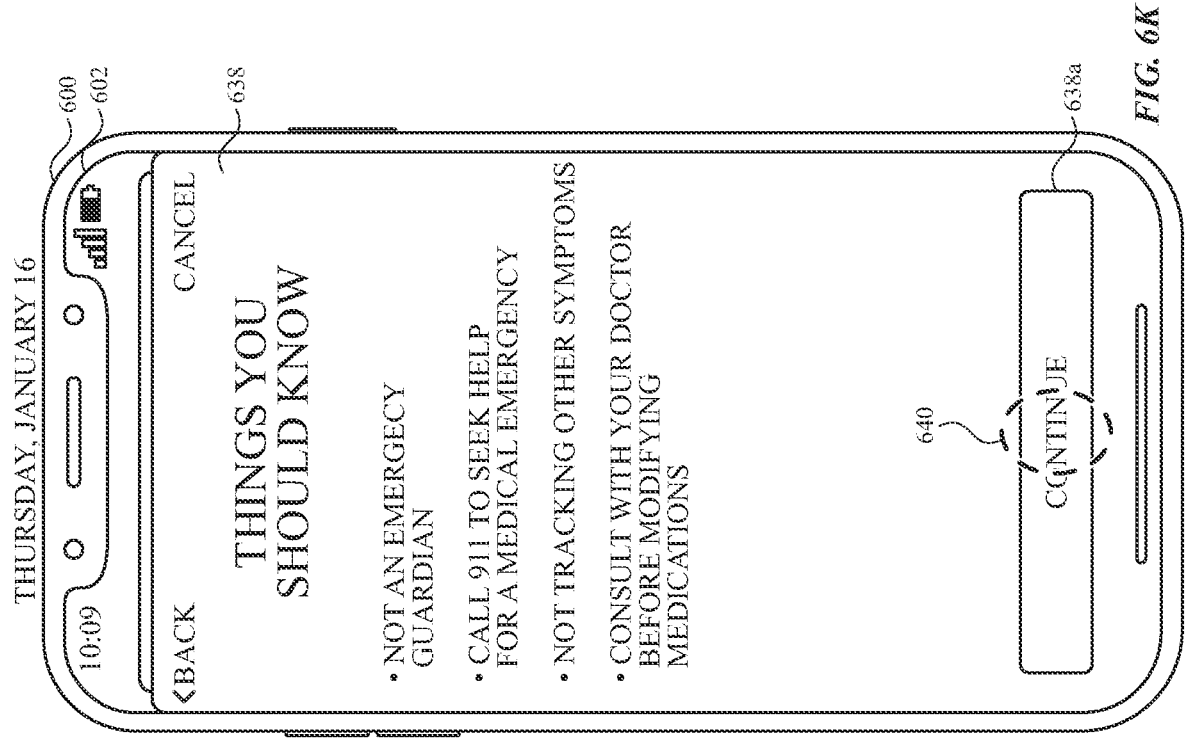
Figure 6N:
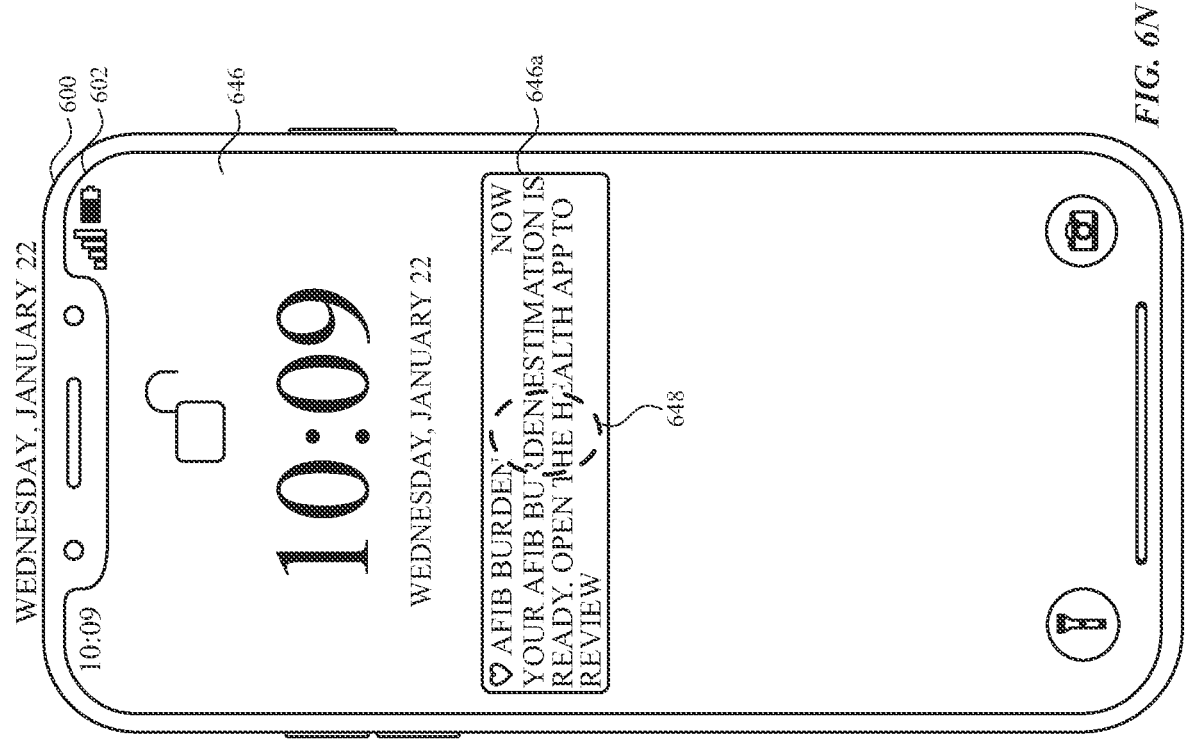

In response to detecting tap input 636, device 600 displays, on touchscreen display 602, precautionary user interface 638, as shown in FIG. 6K. Precautionary user interface 638 explains that the atrial fibrillation burden tracking feature is not a substitute for professional medical services. Device 600 detects tap input 640 corresponding to continue affordance 638a and displays onboarding completion user interface 642 in FIG. 6L.

FIG. 6L depicts device 600 displaying, on touchscreen display 602, onboarding completion user interface 642. Onboarding completion user interface 642 includes instructional prompt 642a that reads, "WEAR YOUR WATCH AND YOUR FIRST ESTIMATE WILL BE READY IN 7 DAYS." In some embodiments, instructional prompt 642a further details how long (e.g. 4, 6, or 8 hours) the external sensor device (e.g., a smart watch, a heart monitor) should be worn per day to gather atrial fibrillation data (e.g., "Wear your watch for at least 6 hours each day for 7 days") before atrial fibrillation burden estimates are available. In some embodiments, the external sensor device must be worn for consecutive days. In some embodiments, the external sensor device can be worn for non-consecutive days. In some embodiments, the external sensor device must be worn for a total number of hours. In some embodiments, atrial fibrillation burden measurements ready in more or less than seven days (e.g., in five days or in two weeks). In some embodiments, if the external sensor device is not worn frequently or consistently enough, device 600 displays a prompt reminding the user to wear the external sensor device. In some embodiments, atrial fibrillation burden measurements are ready after a predetermined number of atrial fibrillation measurements are obtained (e.g., 5 measurements, 10 measurements, 20 measurements) rather than being ready after a predetermined period of time.

Onboarding completion user interface 642 further includes week indicator 642b having 7 letters each representing a day of the week. Within week indicator 642b, "T" for Thursday is circled and corresponds to the current date of THURSDAY, January 16, as shown above device 600. Onboarding completion user interface 642 also includes done affordance 642c. Device 600 detects tap input 644 corresponding to selection of done affordance 642c, which ends the onboarding for atrial fibrillation burden tracking.

Figure 6M:
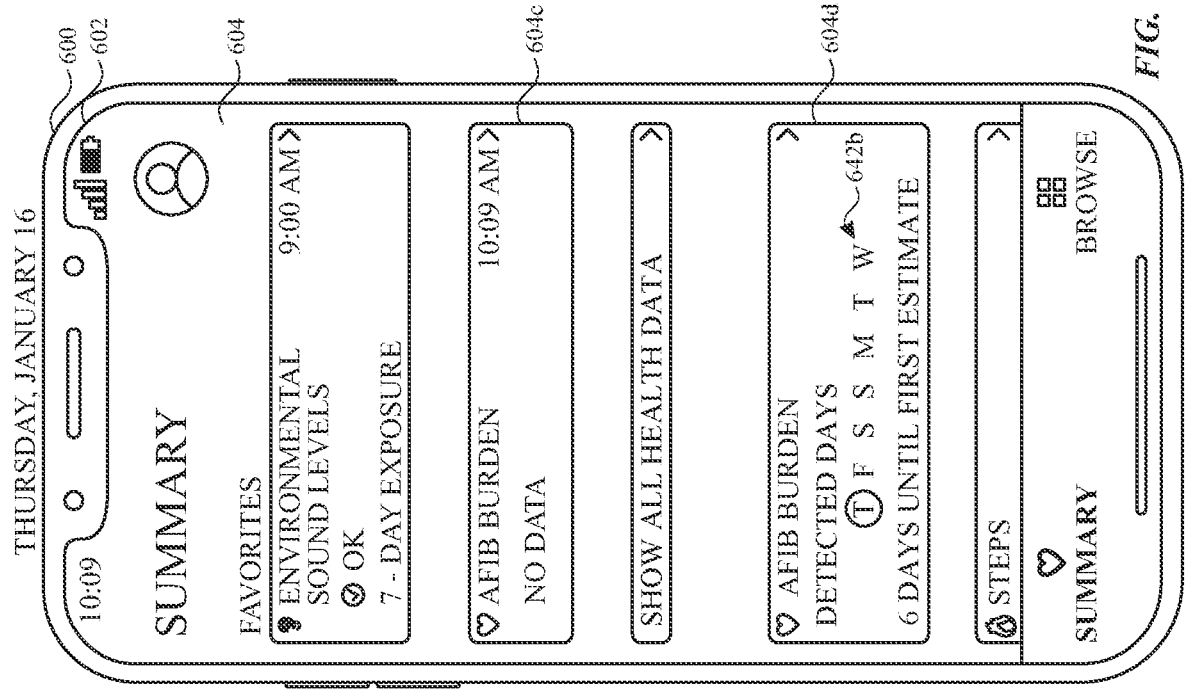

Upon completion of onboarding for atrial fibrillation burden tracking, device 600 displays health application user interface 604 as shown in FIG. 6M. Health application user interface 604 includes a plurality of health-related affordances corresponding to various tracked user data. Specifically, AFib burden affordances 604c and 604d correspond to the atrial fibrillation burden tracking feature. AFib burden affordance 604c includes text "NO DATA" to indicate that atrial fibrillation burden estimates are not yet available. AFib burden affordance 604d includes week indicator 642b, as described above with reference to FIG. 6L, and text "6 DAYS UNTIL FIRST ESTIMATE."

Turning now to FIG. 6N, the current date is WEDNESDAY, January 22, as shown above device 600. Device 600 displays, on touchscreen display 602, lock screen user interface 646 having notification 646a. Notification 646a is displayed when enough atrial fibrillation data has been collected to provide an atrial fibrillation burden estimate. In some embodiments a similar notification is displayed on an external electronic device, such as device 668 of FIGS. 6W-6X. Device 600 detects tap input 648 corresponding to selection of notification 646a. In response to tap input 648, device 600 displays health application user interface 604, as shown in FIG. 6O. In some embodiments, in response to tap input 648, device 600 displays AFib burden data user interface 652 of FIG. 6P.

As shown in FIG. 6O, in response to detecting tap input 648, device 600 displays health application user interface 604 with AFib burden affordances 604c and 604e. AFib burden affordance 604c includes text "64%," which is the first and current atrial fibrillation burden weekly estimate. In some embodiments, as time progresses, AFib burden affordance 604c will include text corresponding to the current atrial fibrillation burden weekly estimate. AFib burden affordance 604e details that additional atrial fibrillation data is needed to view trends in atrial fibrillation burden, as indicated by the text and progress bar having a data collection time period (e.g., six months, January 16 to July 16) and progress indication shown by the hatching on the left side of the progress bar and text "7 DAYS." Trends in atrial fibrillation burden are discussed in more detail, below, with reference to FIG. 6V. In some embodiments, the data collection time period is based on a number of weeks. In some embodiments, the data collection time period is based on a number of days. Device 600 detects touch inputs 650a and 650b corresponding to selection of AFib burden affordances 604c and 604e, respectively. In response to touch inputs 650a and 650b, device 600 displays AFib burden data user interface 652 as shown in FIG. 6P.

Figure 6P:
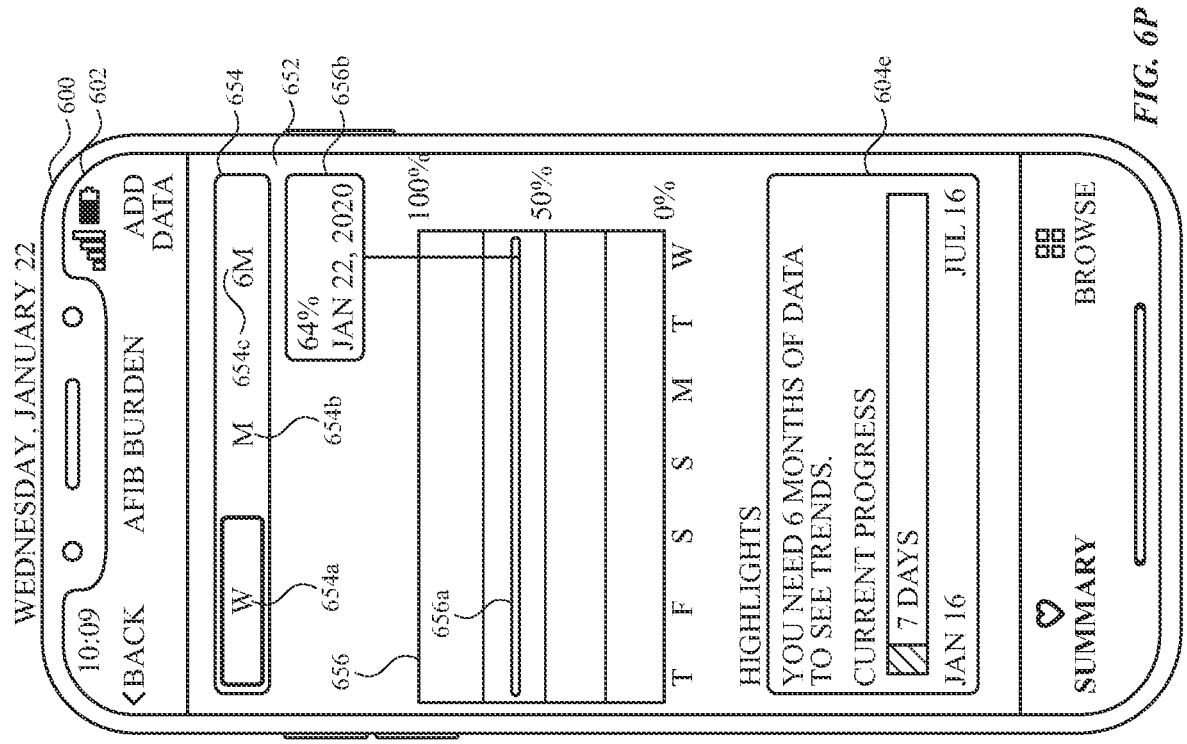
Figure 6O:
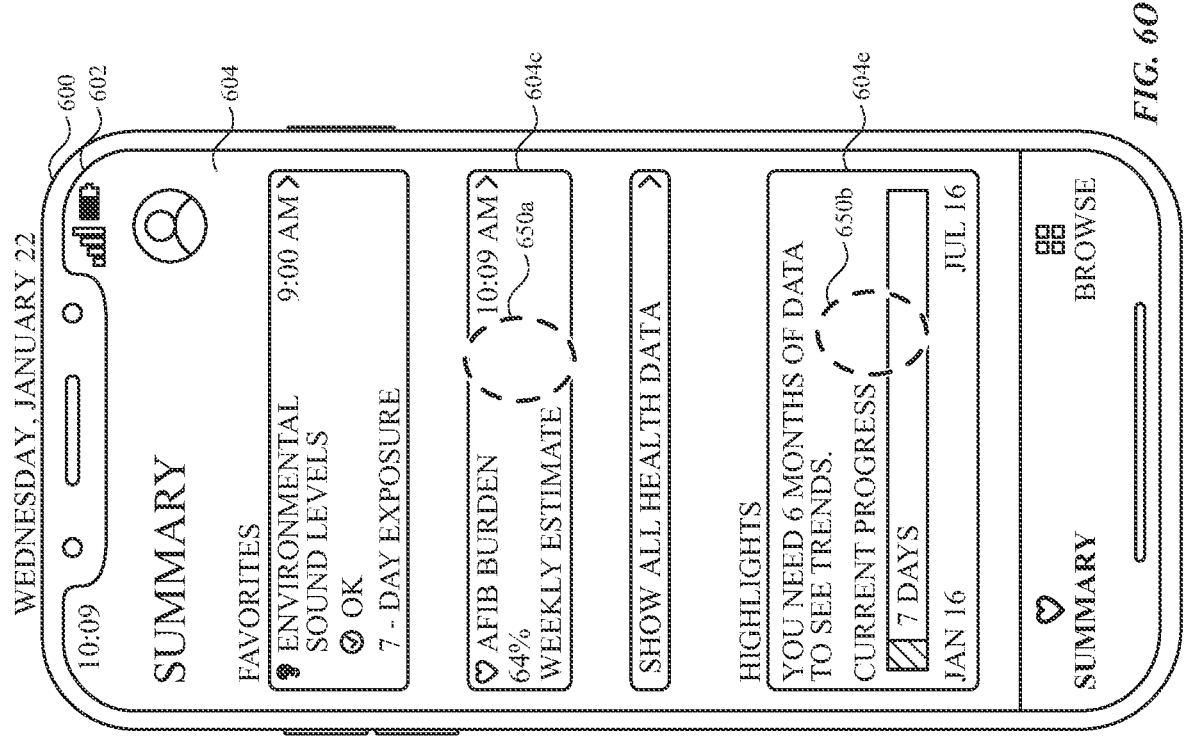

In FIG. 6P, device 600 displays, on touchscreen display 602, AFib burden data user interface 652. AFib burden data user interface 652 includes time period selection affordance 654 (e.g., week, month, six months), graph region 656, and AFib burden affordance 604e of FIG. 6O. Time period selection affordance 654 shows week affordance 654a, month affordance 654b, and six month affordance 654c. Currently, time period selection affordance 654 shows week affordance 654a (e.g., "W") selected, for displaying graph region 656 in a week-long period along the x-axis.

Graph region 656 of FIG. 6P illustrates AFib burden weekly estimate data 656a collected during the week of January 16 to January 22. AFib burden weekly estimate data 656a is 64%, as indicated along the y-axis of percentage of time atrial fibrillation is detected and data selection affordance 656b. Data selection affordance 656b includes the current date, "JAN 22, 2020" and the atrial fibrillation burden weekly estimate of 64%. In some embodiments, data selection affordance 656b is not displayed. In some embodiments, data selection affordance 656b is displayed after device 600 detects a touch input corresponding to selection of a portion of AFib burden weekly estimate data 656a, such as the designation portion of graph 656 corresponding to Wednesday, January 22. In some embodiments, while the single atrial fibrillation burden value of 64% is displayed for the entire week, multiple data points and/or multiple determinations of atrial fibrillation data was collected over the weeklong period. For example, 100 data points may have been collected with 64 data points indicating atrial fibrillation over the week long period.

AFib burden weekly estimate data 656a of graph region 656 in FIG. 6P is 64% for the week-long period. The AFib burden weekly estimate is calculated once per week, based on the previous 7 days of atrial fibrillation data collections. This concept is further illustrated by graph region 656 of FIG. 6Q.

In FIG. 6Q, one month has passed since atrial fibrillation data collection has commenced, as indicated by date SATURDAY, February 15 above device 600. Device 600 displays, on touchscreen display 602, AFib burden data user interface 652. AFib burden data user interface 652 includes time period selection affordance 654, graph region 656, and AFib burden affordance 604e. AFib burden affordance 604e now shows that atrial fibrillation data has been collected for 30 days, as indicated by the hatched, left-side portion of the progress bar. Time period selection affordance 654 now shows month affordance 654b (e.g., "M") selected, and graph region 656 is displayed for a month-long period along the x-axis. AFib burden weekly estimate data 656a spans the portion of the graph corresponding to the week of January 16 to January 22. Graph region 656 further includes AFib burden weekly estimate data for 3 weeks following January 16 to January 22 at various other atrial fibrillation burden estimate values based on the atrial fibrillation data collected for each respective week. In some embodiments, if month affordance 654b (e.g., "M") is selected prior to one month of atrial fibrillation data collection, such as in FIG. 6P, graph region 656 would be shown with AFib burden weekly estimate data 656a spanning the portion of the graph corresponding to the week of January 16 to January 22 and without additional data. Graph region 656 also includes data selection affordance 656*b* corresponding to date "JAN 22, 2020" and the atrial fibrillation burden weekly estimate of 64%, similar to FIG. 6P.

Turning now to FIG. 6R, six months have passed since atrial fibrillation data collection has commenced, as indicated by date THURSDAY, July 16 above device 600. Device 600 displays, on touchscreen display 602, AFib burden data user interface 652. Fib burden data user interface 652 includes time period selection affordance 654 and graph region 656. Time period selection affordance 654 now shows six-month affordance 654*c* (e.g., "6M") selected, and graph region 656 is displayed for a six-month-long period along the x-axis. Instead of showing AFib burden weekly estimate data similar to FIG. 6P and FIG. 6O, graph region 656 includes AFib burden monthly estimate data 656*c*, which is atrial fibrillation burden estimate values based on the atrial fibrillation data collected for each respective month. Data selection affordance 656*b* includes the month "JAN 2020" and the atrial fibrillation burden monthly estimate of 62%. When changing graph region 656 from week or month views (e.g., in FIG. 6P and FIG. 6Q) to the six month view of FIG. 6R, the atrial fibrillation burden estimate changes from a weekly average to a monthly average.

In FIG. 6R, device 600 no longer displays AFib burden affordance 604*e*, since atrial fibrillation data has now been collected for six months. Instead, device 600 displays lifestyle modification affordance 658. Device 600 detects tap input 660 corresponding to selection of lifestyle modification affordance 658. In some embodiments, lifestyle modification affordance 658 is displayed below graph region 656 of FIGS. 6P and 6Q, corresponding to week-long and month-long graphs respectively (e.g., once enough atrial fibrillation has been collected (e.g., after six months)).

As shown in FIG. 6S, in response to detecting tap input 660, device 600 displays, on touchscreen display 602, trend user interface 662. Trend user interface 662 includes range portion 662*a* detailing the AFib burden estimation range and the time period "JAN 16-JUN 30, 2020." In this example, atrial fibrillation data collection began January 16 and the current date is July 16. Device 600 provides a monthly atrial fibrillation estimation for each discrete month, despite the first month being a partial month. In some embodiments, the time period is exactly six months. In some embodiments, trend user interface 662 is displayed having a time period corresponding to the selected time period (e.g., "W" for week, "M" for month, "6M" for six months) on time period selection affordance 654 of AFib burden data user interface 652.

Additionally, trend user interface 662 of FIG. 6S includes AFib burden graph region 662*b*, which corresponds to graph region 656 of FIG. 6R, and lifestyle modification graph region 662*c*. In FIG. 6S, lifestyle modification graph region 662*c* displays the average hours of sleep per month. Sleep is one example of a lifestyle modification factor. The lifestyle modification factors 658*a*-658*d* (e.g., sleep, alcohol, weight, and mindfulness minutes (e.g., time spent meditating)) are displayed below lifestyle modification graph region 662*c*. The lifestyle modification factor 658*a*, corresponding to sleep, is selected. In this example, the first lifestyle modification factor, "SLEEP," is selected by default when device 600 displays trend user interface 662. In some embodiments, device 600 displays trend user interface 662 without a lifestyle modification factor selected, then device 600 detects a tap input corresponding to selection of a lifestyle modification factor and displays lifestyle modification graph region 662*c*. Device 600 detects tap input 663 corresponding to selection of lifestyle modification factor 658*b*, "ALCOHOL."

In FIG. 6T, in response to detecting tap input 663, device 600 modifies trend user interface 662 to display lifestyle modification graph region 662*d*, corresponding to the average number of alcoholic beverages consumed per month, and lifestyle modification factor 658*b*, "ALCOHOL," is selected. As shown by AFib burden graph region 662*b* and lifestyle modification graph region 662*c* of FIG. 6S, an increase in the number of hours spent sleeping correlates to a reduction in atrial fibrillation burden (e.g., the percentage of time spent in atrial fibrillation). Conversely, in FIG. 6T, an increase in the number of alcoholic beverages consumed correlates to an increase in atrial fibrillation burden (e.g., the percentage of time spent in atrial fibrillation). In some embodiments, lifestyle modification factor data is collected by biometric sensors on an electronic device in communication with device 600 (e.g., a smart watch collecting sleep data and/or time spent meditating, a smart scale). In some embodiments, lifestyle modification factor data is input by the user on device 600 (e.g., the time spent sleeping and/or meditating, the number of alcoholic or caffeinated beverages consumed per day).

Figure 6U:
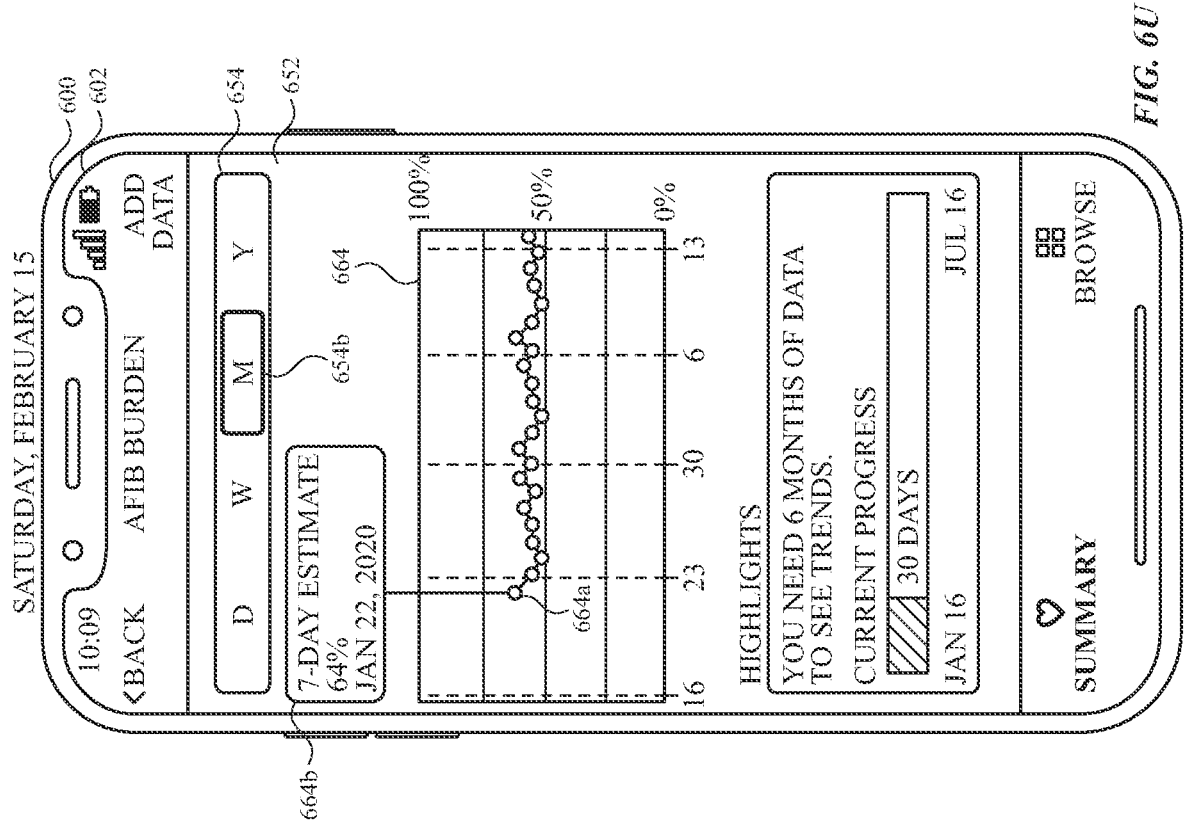

Turning now to FIG. 6U, the current date is SATURDAY, February 15, as shown above device 600, and device 600 displays, on touchscreen display 602, AFib burden data user interface 652. FIG. 6U is an alternate to FIG. 6Q. In some embodiments, device 600 provides an option for displaying atrial burden according to FIG. 6Q or FIG. 6U. Both graph regions show a month-long period along the x-axis for atrial fibrillation burden measurements, as indicated by time period selection affordance 654 having month affordance 654*b* (e.g., "M") selected. Instead of displaying data spanning a week period, like in FIG. 6Q, FIG. 6U illustrates graph region 664 having daily data points based on a rolling 7-day average for atrial fibrillation burden. Data point 664*a* is the average percentage of time spent in atrial fibrillation for the prior seven days, January 16 to January 22. Data selection affordance 664*b* includes the date, "JAN 22, 2020" and the atrial fibrillation burden weekly estimate of 64%. As shown in FIG. 6U, each daily data point is based on data that overlaps with the preceding and proceeding data points. For example, the data point corresponding to January $30^{th}$ (based on January $24^{th}$-$30^{th}$ data) would be based on data that overlaps for 6 out of 7 days with the daily data point for January $29^{th}$ (based on January $23^{rd}$-$29^{th}$ data). In some embodiments, if time period selection affordance 654 has year affordance (e.g., "Y") selected, graph region 664 would display a data point corresponding to each month with 12 months along the x-axis. In some embodiments, if time period selection affordance 654 has week affordance (e.g., "W") selected, graph region 664 would display a data point corresponding to each day, with seven days along the x-axis. In some embodiments, if time period selection affordance 654 has day affordance (e.g., "D") selected, graph region 664 would display a single data point corresponding to a particular day.

Figure 6V:
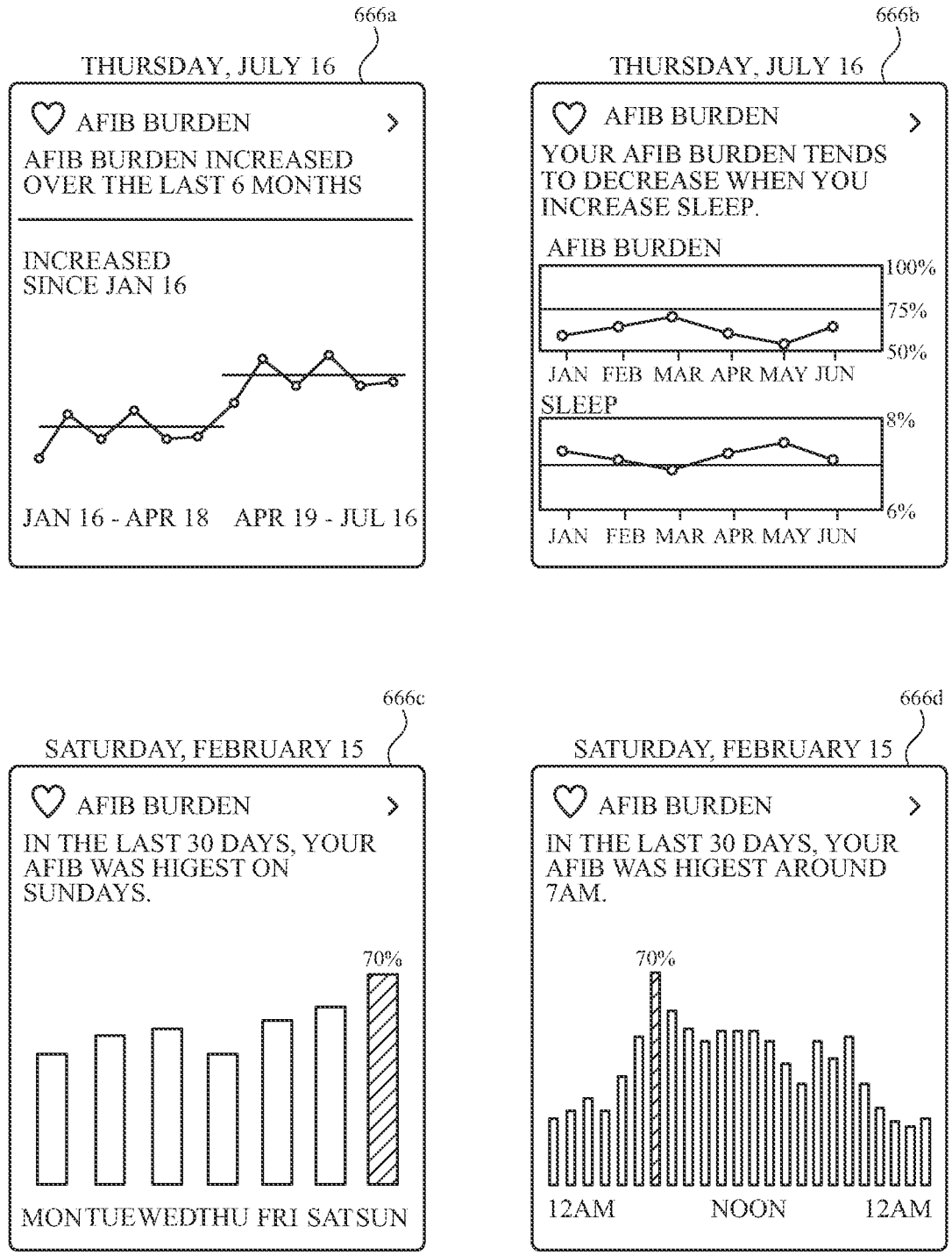

FIG. 6V illustrates various highlight affordances 666*a*-666*d* that can be displayed on health application user interface 604 (e.g., in FIG. 6O) and/or in AFib burden data user interface 652 (e.g., in FIGS. 6P and 6Q). Highlight affordances 666*a* and 666*b* are six month trends that require six months of atrial fibrillation data to be collected before being displayed, as indicated by date, THURSDAY, July 16, above each affordance, which is six months after commencing atrial fibrillation data collection on January 16. Highlight affordance 666a details a trend in atrial fibrillation measurements over six months. Highlight affordance 666b details a trend in atrial fibrillation measurements when compared to lifestyle modification factor sleep over a six month period of time, similar to FIG. 6S. In some embodiments, highlight affordance 666b compares other lifestyle modification factors (e.g., sleep, alcohol consumption, weight, mindfulness minutes, and caffeine intake). In some embodiments, highlight affordances 666a and 666b use time periods other than six months (e.g., one month or one year) to present a trend. In some embodiments, the trends are based on comparing the entire set of atrial fibrillation data for a first time period to the entire set of atrial fibrillation data for a second time period, as is the case for affordances 666a and 666b.

Highlight affordances 666c and 666d ore one month trends that require 30 days or more of atrial fibrillation data to be collected before being displayed, as indicated by date, SATURDAY, February 15, above each affordance, which is 30 days after commencing atrial fibrillation data collection on January 16. Highlight affordance 666c details a trend in atrial fibrillation measurements on a day-per-week basis for a 30-day period. Highlight affordance 666d details a trend in atrial fibrillation measurements on an hourly basis for a 30-day period. In some embodiments, highlight affordances 666c and 666d use time periods other than six months to present a trend. In some embodiments, the trends are based on comparing the a recurring subset (e.g., a day of the week or a time of day) of atrial fibrillation data for a first time period to a recurring subset of atrial fibrillation data for a second time period, as is the case for affordances 666c and 666d.

Figure 6W:
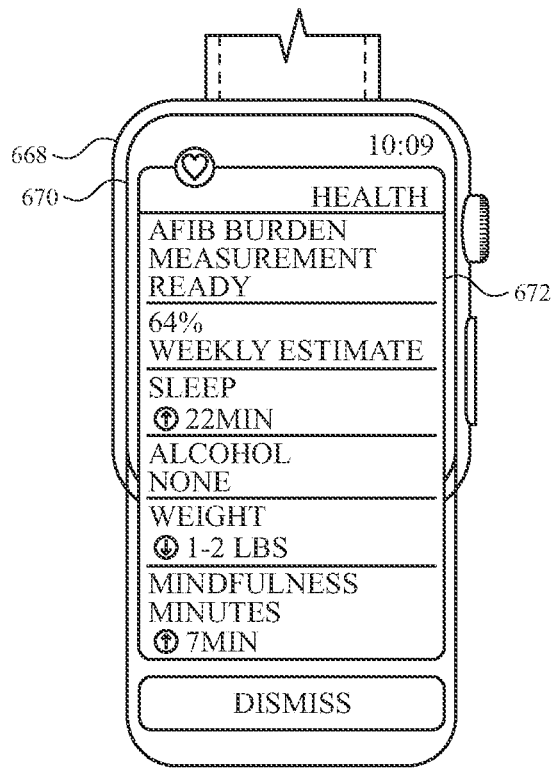

Turning now to FIG. 6W, electronic device 668 is a smart watch connected to device 600. Device 668 displays, on touchscreen display 670, AFib burden measurement notification 672. AFib burden measurement notification 672 includes the weekly estimate for atrial fibrillation burden along with weekly trends in lifestyle modification factors, such as an increase in sleep by 22 minutes, as indicated by the up arrow. In some embodiments, additional lifestyle modification factors are included, such as caffeine intake.

Figure 6X:
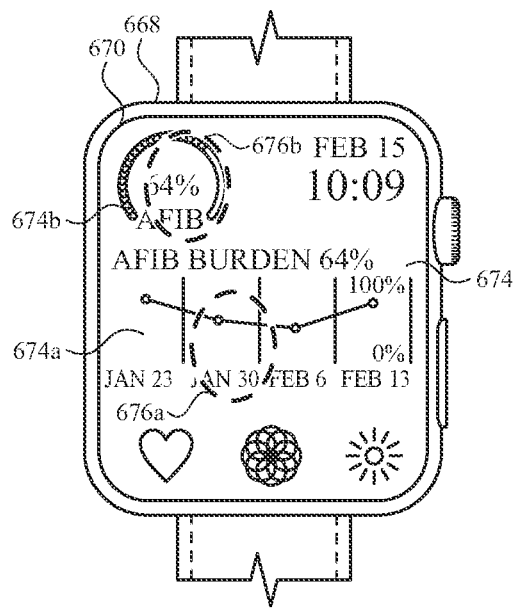
Figure 6Y:
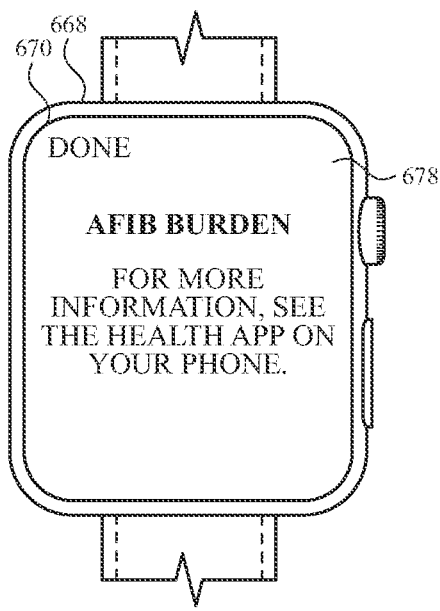

In FIG. 6X, device 668 displays watch face user interface 674 on touchscreen display 670. Watch face user interface 674 includes the current date "FEB 15," time "10:09," and various complication affordances. AFib burden complication affordances 674a and 674b include information about the current atrial fibrillation burden estimate, "64%." AFib burden complication affordance 674a is a reduced size line graph similar to graph region 656 of FIG. 6Q. Device 668 detects tap inputs 676a and 676b corresponding to selection of AFib burden complication affordances 674a and 674b, respectively.

In response to detecting either tap input 676a or 676b, device 668 displays, on touchscreen display 670, AFib burden watch user interface 678 in FIG. 6Y. AFib burden watch user interface 678 includes text directing the user to review the Health App (e.g., the health application user interface 604) on their phone (e.g., device 600) for more information about atrial fibrillation burden. In some embodiments, in response to a tap input on AFib burden measurement notification 672 of FIG. 6W, device 668 displays AFib burden watch user interface 678.

FIG. 7 is a flow diagram illustrating a method for displaying atrial fibrillation data using an electronic device in accordance with some embodiments. Method 700 is performed at a device (e.g., 100, 300, 500, 600, 668) with a display. Some operations in method 700 are, optionally, combined, the orders of some operations are, optionally, changed, and some operations are, optionally, omitted.

In some embodiments, the electronic device (e.g., 600, 668) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 700 provides an intuitive way for displaying atrial fibrillation data. The method reduces the cognitive burden on a user for displaying atrial fibrillation data, thereby creating a more efficient human-machine interface. For battery-operated computing devices, enabling a user to displaying atrial fibrillation data faster and more efficiently conserves power and increases the time between battery charges.

In method 700, the computer system (e.g., 600, 668), displays (702), via the display generation component (e.g., 602, 670), a user interface (e.g., 662) (e.g., an interface of a health application; a heart health interface) that includes (In some embodiments, that concurrently displays) a first representation (e.g., 662b) (e.g., textual representation and/or a graphical representation) of received (e.g., detected (e.g., via sensors in communication with the computer system), inputted, and/or transmitted) atrial fibrillation (e.g., AFib or AF) data (e.g., data pertaining to detected atrial fibrillation (e.g., a quantification of atrial fibrillation events/incidents; a duration of the longest detected atrial fibrillation event); atrial fibrillation burden data (e.g., a percentage and/or proportion of the time that subject experiences atrial fibrillation; the number of atrial fibrillation measurements over the total number of measurements)) for a (e.g., determined over the first time period) first time period (e.g., depicted in 662a) (e.g., a predetermined number of days, a week, a month); and (in some embodiments, the representation is generated based on a plurality of measurements and/or values of atrial fibrillation-related data obtained over the first time period (e.g., the representation is a calculated and/or derived value) .) a first representation (e.g., 662c, 662d, 658a, 658b, 658c, 658d) (e.g., textual representation and/or a graphical representation) of received (e.g., detected (e.g., via sensors in communication with the computer system), inputted, and/or transmitted) non-heart data (e.g., data that is not a measurement of a property or parameter (e.g., heart rate data, atrial fibrillation data, ejection fraction data; electrocardiogram data) of a subject's heart or the function of the subject's heart; data relating to behaviors (e.g., habits) of a user (e.g., behaviors that can have an effect on atrial fibrillation)) for the (e.g., determined over the first time period) first time period. In some embodiments, providing the representations of the atrial fibrillation data and the non-heart data in the same user interface allows a user to determine the effect of the non-heart data on atrial fibrillation (e.g., on atrial fibrillation burden)). Displaying a user interface with representations of atrial fibrillation data for a first time period and non-heart data for the same first time period provides the user with feedback as to the state of data for the same time period received by the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first representation (e.g., 662b) of received atrial fibrillation data is a representation (e.g., a percentile; a numerical fraction; a ratio) of the proportion of time that a subject (e.g., a user of the computer system; an individual to whom the data pertains) is in atrial fibrillation during the first time period (e.g., an atrial fibrillation burden value and/or score). In some embodiments, the representation is calculated as a percentage of measurement samples that are classified (e.g., by the computer system; by a clinical standard) as being in atrial fibrillation in the sample of total measurement samples (e.g., 10%, 20%, 30%, 40%, or 50% atrial fibrillation burden). Displaying a representation of time that a subject is in atrial fibrillation during the first time period provides the user with additional feedback as a subset of the received data compared to the entirety of the received data. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the computer system receives (704) data that corresponds to an atrial fibrillation event (e.g., biometric sensor data that is determined by the computer system to be indicative of an atrial fibrillation event; and/or data from an external electronic device (e.g., a connected smart watch) that corresponds to an atrial fibrillation event (e.g., notification data indicating an AFib event; biometric sensor data corresponding to an AFib event)). In response to receiving the data that corresponds to an atrial fibrillation event and in accordance with a determination that a set of atrial fibrillation event notification criteria are met, the computer system outputs (706) a notification (e.g., a system-generated alert that does not require specific/explicit user input, per notification, to output) indicating that an atrial fibrillation event has occurred (e.g., has been detected by the computer system and/or by an electronic device connected to the computer system). In response to receiving the data that corresponds to an atrial fibrillation event and in accordance with a determination that the set of atrial fibrillation event notification criteria are not met, the computer system forgoes outputting (708) the notification indicating that an atrial fibrillation event has occurred, wherein the set of atrial fibrillation event notification criteria are not met when the computer system is configured to receive (e.g., detect; collect; and/or track data from an external electronic device and/or a connected or integrated sensor) atrial fibrillation data without outputting notifications indicating that an atrial fibrillation event has occurred. In some embodiments, when the computer system is configured to track AFib burden, the computer system does not issue AFib notifications for discrete AFib events. Automatically forgoing output of notifications of discrete AFib events when the computer system is configured to do so reduces the need for user input to eliminate such notifications, while still collecting atrial fibrillation data. In some embodiments, when the data includes frequent atrial fibrillation events, doing so can also reduce the number of notifications, thereby saving device power and processing resources. Performing an operation when a set of conditions are met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, at least a portion of the atrial fibrillation data represented by the first representation (e.g., 662b) of received atrial fibrillation data is received from (e.g., provided by) an external electronic device (e.g., 668) (e.g., a device having one or more biometric sensors for collecting atrial fibrillation data (e.g., a smart watch)) in communication with the computer system. The computer system, prior to displaying the user interface (e.g., 662), displays (e.g., displaying as a system-generated alert; displaying in response to a user input requesting display of the indication) an indication (e.g., 642a, 642b) of one or more conditions that are to be met before the user interface is available for display, wherein the one or more conditions includes a first condition that is based on a period of time remaining (e.g., 7 days) before the one or more conditions are met (e.g., a period of time remaining in the first time period; a period of time during which the external electronic device is configured (e.g., by being worn) to gather atrial fibrillation data from the user of the external electronic device). Displaying an indication an indication of one or more conditions that are to be met before the user interface is available for display provides the user with feedback as to the state of the function and what is required to display the user interface. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the user interface further includes a second representation (e.g., the atrial fibrillation burden value for February in FIG. 6S) of received atrial fibrillation data (e.g., data pertaining to detected atrial fibrillation (e.g., a quantification of atrial fibrillation events/incidents; a duration of the longest detected atrial fibrillation event); atrial fibrillation burden data (e.g., a percentage and/or proportion of the time that subject experiences atrial fibrillation; the number of atrial fibrillation measurements over the total number of measurements)) for a second time period (e.g., February in FIG. 6S), different from the first time period (e.g., a predetermined number of days, a week, a month; a period of time that overlaps with the first time period; a period of time that does not overlap with the first time period (e.g., a consecutive period of time; a period of time that has the same duration as the first time period). In some embodiments, the first and second representation are displayed together as part of a graph of AFib data over multiple time periods; and a second representation (e.g., sleep data for February in FIG. 6S) of received non-heart data for the second time period. Displaying a representation of received atrial fibrillation data for a second time period in the user interface provides the user with feedback as data received for that second time period. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the computer system displays (e.g., as part of the user interface; separate from the user interface) received atrial fibrillation data for the first time period and the second time period; and received non-heart data for the first time period and the second time period. The computer system determines (e.g., based on the data shown in FIG. 6T) whether a change in the received non-heart data between the first time period and the second time period has a numerical relationship (in some embodiments, a correlation) with a change in the received atrial fibrillation data between the first time period and the second time period. In some embodiments, the indication is also based on a change in the atrial fibrillation data between the first time period and the second time period. In some embodiments, the indication is an amount of change in the non-heart data and the corresponding amount of change in the atrial fibrillation data. In some embodiments, also displaying a representation of a relationship (e.g., a calculated and/or predicted correlation or causal relationship between the non-heart data and the atrial fibrillation data) between the atrial fibrillation data and the non-heart data. Displaying a representation of a relationship between the atrial fibrillation and non-heart data for both the first and second time periods provides the user with a more detailed understanding of the data received by the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first representation of received data is provide as graphed data (e.g., as a bar or line graph).

In some embodiments, the first time period and the second time period do not overlap (e.g., as shown for the first week and the second week of FIG. 6Q) (e.g., are consecutive, non-overlapping time periods of the same duration (e.g., a first week and the subsequent week)). Displaying representations of data for first and second time periods that do not overlap provides the user with discrete visualizations of the data and provides independent feedback as to received data, without intermingling. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first time period and the second time period partially overlap (e.g., as shown for day 29 and day 30 in FIG. 6U) (e.g., are rolling averages of a time subset of a recurring duration (e.g., week-long rolling averages that differ in one day (e.g., an average of days 1-7 and an average of days 2-8))). Displaying representations of data for first and second time periods that overlap provides the user with an increased number of representations for a given period of time and provides additional feedback as to received data and the relationships between the data for the two interrelated time periods. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first representation (e.g., 662c, 658a) of received non-heart data is a representation of one or more data types for a subject (e.g., a user of the computer system; an individual to whom the data pertains) selected from the group consisting of sleep data (e.g., hours of sleep), alcohol consumption data (e.g., number of alcoholic drinks in the time period), weight (e.g., body weight) data, stress management data (e.g., meditation and/or mindfulness minutes), and caffeine consumption data (e.g., number of caffeinated drinks in the time period).

In some embodiments, the computer system displays (e.g., as part of the user interface; separate from the user interface) an indication (e.g., 666a, 666b) of a trend (e.g., a change; a delta; a prediction and/or extrapolation of a pattern in the data; an indication of whether the data is trending up or trending down) in received non-heart data for the first time period (e.g., April 19-July 20 in 666a) and a third time period (e.g., January 16-April 18 in 666a) that preceded the first time period (e.g., a consecutive, previous time period). Displaying an indication of a trend for the received non-heart data provides the user with a more detailed understanding of the data received by the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first representation (e.g., 662c, 658a) of received non-heart data for the first time period is a representation of a first type of received non-heart data (e.g., sleep data) and wherein the user interface includes a first selectable user interface object (e.g., 658b, 658c, 658d) that corresponds to a second type of received non-heart data different from the first type of received non-heart data (e.g., alcohol consumption data). The computer system, while the first representation of received non-heart data for the first time period is displayed, receives a first user input (e.g., a tap) corresponding to the first selectable user interface object. In response to receiving the first user input, the computer system displays a third representation (e.g., 662d) (e.g., textual representation and/or a graphical representation) of received non-heart data (e.g., data for the first time period) that is a representation of the second type of received non-heart data. Displaying an additional representation of received non-heart data in response to selection of a user interface object provides the user with more control of the device and what is displayed. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system, in response to receiving the first user input (e.g., the input of FIG. 6S), ceases to display the first representation (e.g., 662c) of received non-heart data for the first time period. In some embodiments, the second representation of received non-heart data replaces the first representation of received non-heart data. Ceasing to display the first representation in response to the first user input reduces cluttering of the user interface and focuses attention on the additional representation of the non-heart data. Reducing clutter of the user interface and providing improved focus on requested data enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system, prior to displaying the user interface that include the first representation (e.g., 662b) of received atrial fibrillation data for the first time period and the first representation (e.g., 662c) of received non-heart data for the first time period, displays a second user interface (e.g., 652 of FIG. 6R) that includes (In some embodiments, the second user interface does not include any representation of received non-heart data) a third representation (e.g., 656) (e.g., a representation that is the same as the first representation) of received atrial fibrillation data for the first time period; and a second selectable user interface object (e.g., 658); wherein displaying the user interface occurs in response to receiving a second user input (e.g., 660) corresponding to the second selectable user interface object. In some embodiments, the user interface replaces the second user interface; in some embodiments, the second user interface is modified to result in display of the user interface. Displaying the user interface in response to selection of a user interface object provides the user with more control of the device and what is displayed. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the received non-health data of the first representation (e.g., 662c) of received non-health data for the first time period is data collected via one or more sensors (e.g., sensors in communication with the computer system; sensors integrated into the computer system; sensors integrated into an electronic device (e.g., a smart watch) that is in communication with the computer system).

In some embodiments, the received non-health data of the first representation (e.g., 662c) of received non-health data for the first time period is user-inputted data (e.g., inputted at the computer system; inputted at an external electronic device (e.g., a smart watch) in communication with the computer system).

In some embodiments, the first representation (e.g., 658a) of received non-heart data for the first time period is a representation of a third type of received non-heart data (e.g., that is the same as the first type; that is different than the first type (e.g., sleep data)); and the user interface includes a third representation (658b) of received non-heart data for the first time period that is a representation of a fourth type of received non-heart data different from the third type of received non-heart data (e.g., alcohol consumption data). Displaying representations of multiple types of non-health data in the user interface provides the user with feedback as to the state of data for the same time period received by the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first representation (e.g., 662c, 662d) of received non-heart data for the first time period is a data chart (e.g., a pie chart; a line graph; a bar graph). In some embodiments, the received non-heart data is represented in the user interface both as a data chart and as a numerical value that is not a data chart.

In some embodiments, the computer system displays (e.g., in the user interface; separate from the user interface) a representation (e.g., 666a, 666b, 666c, 666d) of a derived atrial fibrillation data value that is based, at least in part, on the received atrial fibrillation data for the first time period and received atrial fibrillation data for a fourth time period that is different than the first time period (e.g., a value representing a determined or calculated relationship (e.g., a mathematical relationship (e.g., a change; a difference; an average; a comparison of one recurring subset (e.g., a day of the week; a time of day) of the first time period to a related subset of the fourth time period) between the atrial fibrillation data for the first time period and at least the atrial fibrillation data for the fourth time period). Displaying a representation of a derived atrial fibrillation data value provides the user with a more detailed understanding of the data received by the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the computer system, prior to displaying the representation (e.g., 666a, 666b, 666c, 666d) of a derived atrial fibrillation data value, displays an indication (e.g., 604e) (e.g., a progress indicator) of progress towards collection of a quantity of atrial fibrillation data that is to be collected before displaying the representation of a derived atrial fibrillation data value. In some embodiments, the indication includes an amount of remaining time and/or a predicted time (e.g., a date) by which sufficient data will have been collected. Displaying an indication (e.g., a progress indicator) of progress towards collection of a quantity of atrial fibrillation data provides the user with feedback as to the state of the function and what is required to display the representation of a derived atrial fibrillation data value. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the derived atrial fibrillation data value (e.g., 666a, 666b) is a comparison (e.g., a quantitative comparison of a change and/or trend) of the received atrial fibrillation data for the first time period and the received atrial fibrillation data for the fourth time period (e.g., a comparison of the data for the entire first time period compared to the data for the entire second time period).

In some embodiments, the derived atrial fibrillation data value (e.g., 666a, 666b, 666c, 666d) is based on a comparison of a recurring sub-period of time (e.g., a sub-set; a day of the week (e.g., Mondays); a time of day (e.g., mornings of each day of the time period)) in the first time period and the second time period.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the display of atrial fibrillation data. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted health content that is of greater interest to the user. Accordingly, use of such personal information data enables users to have calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide health-associated data for targeted content delivery services. In yet another example, users can select to limit the length of time health-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A computer system, comprising:
a display generation component;
one or more input devices;
one or more processors; and
memory storing one or more programs configured to be executed by the one or more processors, the one or more programs including instructions for:
displaying, via the display generation component, a user interface that includes:
a first representation of received atrial fibrillation data for a first time period; and
a first representation of received non-heart data for the first time period;
receiving, via one or more biometric sensors in communication with the computer system for collecting atrial fibrillation data, data that corresponds to an atrial fibrillation event;
in response to receiving the data that corresponds to an atrial fibrillation event:
in accordance with a determination that a set of atrial fibrillation event notification criteria are met, wherein the set of atrial fibrillation event notification criteria includes a criterion that is met when the computer system is not configured to track a proportion of time that a subject is in atrial fibrillation during the first time period, outputting a notification indicating that an atrial fibrillation event has occurred; and
in accordance with a determination that the set of atrial fibrillation event notification criteria are not met, forgoing outputting the notification indicating that an atrial fibrillation event has occurred.

2. The computer system of claim 1, wherein at least a portion of the atrial fibrillation data represented by the first representation of received atrial fibrillation data is received from an external electronic device in communication with the computer system, the one or more programs further include instructions for:
prior to displaying the user interface, displaying an indication of one or more conditions that are to be met before the user interface is available for display, wherein the one or more conditions includes a first condition that is based on a period of time remaining before the one or more conditions are met.

3. The computer system of claim 1, wherein the user interface further includes:
a second representation of received atrial fibrillation data for a second time period, different from the first time period; and
a second representation of received non-heart data for the second time period.

4. The computer system of claim 3, wherein the one or more programs further include instructions for:
displaying:
received atrial fibrillation data for the first time period and the second time period;
received non-heart data for the first time period and the second time period; and
determining whether a change in the received non-heart data between the first time period and the second time period has a numerical relationship with a change in the received atrial fibrillation data between the first time period and the second time period.

5. The computer system of claim 3, wherein the first time period and the second time period do not overlap.

6. The computer system of claim 3, wherein the first time period and the second time period partially overlap.

7. The computer system of claim 1, wherein the first representation of received non-heart data is a representation of one or more data types for a subject selected from the group consisting of sleep data, alcohol consumption data, weight data, stress management data, and caffeine consumption data.

8. The computer system of claim 1, wherein the one or more programs further include instructions for:
displaying an indication of a trend in received non-heart data for the first time period and a third time period that preceded the first time period.

9. The computer system of claim 1, wherein the first representation of received non-heart data for the first time period is a representation of a first type of received non-heart data and wherein the user interface includes a first selectable user interface object that corresponds to a second type of received non-heart data different from the first type of received non-heart data, the one or more programs further include instructions for:
while the first representation of received non-heart data for the first time period is displayed, receiving a first user input corresponding to the first selectable user interface object; and
in response to receiving the first user input, displaying a third representation of received non-heart data that is a representation of the second type of received non-heart data.

10. The computer system of claim 9, wherein the one or more programs further include instructions for:
in response to receiving the first user input, ceasing to display the first representation of received non-heart data for the first time period.

11. The computer system of claim 1, wherein the one or more programs further include instructions for:
prior to displaying the user interface that include the first representation of received atrial fibrillation data for the first time period and the first representation of received non-heart data for the first time period, displaying a second user interface that includes:
a third representation of received atrial fibrillation data for the first time period; and
a second selectable user interface object; and
wherein displaying the user interface occurs in response to receiving a second user input corresponding to the second selectable user interface object.

12. The computer system of claim 1, wherein the received non-heart data of the first representation of received non-heart data for the first time period is data collected via one or more sensors.

13. The computer system of claim 1, wherein the received non-heart data of the first representation of received non-heart data for the first time period is user-inputted data.

14. The computer system of claim 1, wherein:
the first representation of received non-heart data for the first time period is a representation of a third type of received non-heart data; and the user interface includes a third representation of received non-heart data for the first time period that is a representation of a fourth type of received non-heart data different from the third type of received non-heart data.

15. The computer system of claim 1, wherein the first representation of received non-heart data for the first time period is a data chart.

16. The computer system of claim 1, wherein the one or more programs further include instructions for:
displaying a representation of a derived atrial fibrillation data value that is based, at least in part, on the received atrial fibrillation data for the first time period and received atrial fibrillation data for a fourth time period that is different than the first time period.

17. The computer system of claim 16, wherein the one or more programs further include instructions for:
prior to displaying the representation of a derived atrial fibrillation data value, displaying an indication of progress towards collection of a quantity of atrial fibrillation data that is to be collected before displaying the representation of a derived atrial fibrillation data value.

18. The computer system of claim 16, wherein the derived atrial fibrillation data value is a comparison of the received atrial fibrillation data for the first time period and the received atrial fibrillation data for the fourth time period.

19. The computer system of claim 16, wherein the derived atrial fibrillation data value is based on a comparison of a recurring sub-period of time in the first time period and the fourth time period.

20. A method, comprising:
at a computer system that is in communication with a display generation component and one or more input devices:
displaying, via the display generation component, a user interface that includes:
a first representation of received atrial fibrillation data for a first time period; and
a first representation of received non-heart data for the first time period;
receiving, via one or more biometric sensors in communication with the computer system for collecting atrial fibrillation data, data that corresponds to an atrial fibrillation event;
in response to receiving the data that corresponds to an atrial fibrillation event:
in accordance with a determination that a set of atrial fibrillation event notification criteria are met, wherein the set of atrial fibrillation event notification criteria includes a criterion that is met when the computer system is not configured to track a proportion of time that a subject is in atrial fibrillation during the first time period, outputting a notification indicating that an atrial fibrillation event has occurred; and
in accordance with a determination that the set of atrial fibrillation event notification criteria are not met, forgoing outputting the notification indicating that an atrial fibrillation event has occurred.

21. The method of claim 20, wherein at least a portion of the atrial fibrillation data represented by the first representation of received atrial fibrillation data is received from an external electronic device in communication with the computer system, the method further comprising:
prior to displaying the user interface, displaying an indication of one or more conditions that are to be met before the user interface is available for display, wherein the one or more conditions includes a first condition that is based on a period of time remaining before the one or more conditions are met.

22. The method of claim 20, wherein the user interface further includes:
a second representation of received atrial fibrillation data for a second time period, different from the first time period; and
a second representation of received non-heart data for the second time period.

23. The method of claim 22, further comprising:
displaying:
received atrial fibrillation data for the first time period and the second time period; and
received non-heart data for the first time period and the second time period; and
determining whether a change in the received non-heart data between the first time period and the second time period has a numerical relationship with a change in the received atrial fibrillation data between the first time period and the second time period.

24. The method of claim 22, wherein the first time period and the second time period do not overlap.

25. The method of claim 22, wherein the first time period and the second time period partially overlap.

26. The method of claim 20, wherein the first representation of received non-heart data is a representation of one or more data types for a subject selected from the group consisting of sleep data, alcohol consumption data, weight data, stress management data, and caffeine consumption data.

27. The method of claim 20, further comprising:
displaying an indication of a trend in received non-heart data for the first time period and a third time period that preceded the first time period.

28. The method of claim 20, wherein the first representation of received non-heart data for the first time period is a representation of a first type of received non-heart data and wherein the user interface includes a first selectable user interface object that corresponds to a second type of received non-heart data different from the first type of received non-heart data, the method further comprising:
while the first representation of received non-heart data for the first time period is displayed, receiving a first user input corresponding to the first selectable user interface object; and
in response to receiving the first user input, displaying a third representation of received non-heart data that is a representation of the second type of received non-heart data.

29. The method of claim 28, further comprising:
in response to receiving the first user input, ceasing to display the first representation of received non-heart data for the first time period.

30. The method of claim 20, further comprising:
prior to displaying the user interface that include the first representation of received atrial fibrillation data for the first time period and the first representation of received non-heart data for the first time period, displaying a second user interface that includes:
a third representation of received atrial fibrillation data for the first time period; and
a second selectable user interface object; and
wherein displaying the user interface occurs in response to receiving a second user input corresponding to the second selectable user interface object.

31. The method of claim 20, wherein the received non-heart data of the first representation of received non-heart data for the first time period is data collected via one or more sensors.

32. The method of claim 20, wherein the received non-heart data of the first representation of received non-heart data for the first time period is user-inputted data.

33. The method of claim 20, wherein:
the first representation of received non-heart data for the first time period is a representation of a third type of received non-heart data; and
the user interface includes a third representation of received non-heart data for the first time period that is a representation of a fourth type of received non-heart data different from the third type of received non-heart data.

34. The method of claim 20, wherein the first representation of received non-heart data for the first time period is a data chart.

35. The method of claim 20, further comprising:
displaying a representation of a derived atrial fibrillation data value that is based, at least in part, on the received atrial fibrillation data for the first time period and received atrial fibrillation data for a fourth time period that is different than the first time period.

36. The method of claim 35, further comprising:
prior to displaying the representation of a derived atrial fibrillation data value, displaying an indication of progress towards collection of a quantity of atrial fibrillation data that is to be collected before displaying the representation of a derived atrial fibrillation data value.

37. The method of claim 35, wherein the derived atrial fibrillation data value is a comparison of the received atrial fibrillation data for the first time period and the received atrial fibrillation data for the fourth time period.

38. The method of claim 35, wherein the derived atrial fibrillation data value is based on a comparison of a recurring sub-period of time in the first time period and the fourth time period.

39. A non-transitory computer-readable storage medium storing one or more programs configured to be executed by one or more processors of a computer system in communication with a display generation component and one or more input devices, the one or more programs including instructions for:
displaying, via the display generation component, a user interface that includes:
a first representation of received atrial fibrillation data for a first time period; and
a first representation of received non-heart data for the first time period;
receiving, via one or more biometric sensors in communication with the computer system for collecting atrial fibrillation data, data that corresponds to an atrial fibrillation event;
in response to receiving the data that corresponds to an atrial fibrillation event:
in accordance with a determination that a set of atrial fibrillation event notification criteria are met, wherein the set of atrial fibrillation event notification criteria includes a criterion that is met when the computer system is not configured to track a proportion of time that a subject is in atrial fibrillation during the first time period, outputting a notification indicating that an atrial fibrillation event has occurred; and
in accordance with a determination that the set of atrial fibrillation event notification criteria are not met, forgoing outputting the notification indicating that an atrial fibrillation event has occurred.

40. The non-transitory computer-readable storage medium of claim 39, wherein at least a portion of the atrial fibrillation data represented by the first representation of received atrial fibrillation data is received from an external electronic device in communication with the computer system, the one or more programs further include instructions for:
prior to displaying the user interface, displaying an indication of one or more conditions that are to be met before the user interface is available for display, wherein the one or more conditions includes a first condition that is based on a period of time remaining before the one or more conditions are met.

41. The non-transitory computer-readable storage medium of claim 39, wherein the user interface further includes:
a second representation of received atrial fibrillation data for a second time period, different from the first time period; and
a second representation of received non-heart data for the second time period.

42. The non-transitory computer-readable storage medium of claim 41, wherein the one or more programs further include instructions for:
displaying:
received atrial fibrillation data for the first time period and the second time period; and
received non-heart data for the first time period and the second time period; and
determining whether a change in the received non-heart data between the first time period and the second time period has a numerical relationship with a change in the received atrial fibrillation data between the first time period and the second time period.

43. The non-transitory computer-readable storage medium of claim 41, wherein the first time period and the second time period do not overlap.

44. The non-transitory computer-readable storage medium of claim 41, wherein the first time period and the second time period partially overlap.

45. The non-transitory computer-readable storage medium of claim 39, wherein the first representation of received non-heart data is a representation of one or more data types for a subject selected from the group consisting of sleep data, alcohol consumption data, weight data, stress management data, and caffeine consumption data.

46. The non-transitory computer-readable storage medium of claim 39, wherein the one or more programs further include instructions for:
displaying an indication of a trend in received non-heart data for the first time period and a third time period that preceded the first time period.

47. The non-transitory computer-readable storage medium of claim 39, wherein the first representation of received non-heart data for the first time period is a representation of a first type of received non-heart data and wherein the user interface includes a first selectable user interface object that corresponds to a second type of received non-heart data different from the first type of received non-heart data, the one or more programs further include instructions for:

while the first representation of received non-heart data for the first time period is displayed, receiving a first user input corresponding to the first selectable user interface object; and in response to receiving the first user input, displaying a third representation of received non-heart data that is a representation of the second type of received non-heart data.

48. The non-transitory computer-readable storage medium of claim 47, wherein the one or more programs further include instructions for:

in response to receiving the first user input, ceasing to display the first representation of received non-heart data for the first time period.

49. The non-transitory computer-readable storage medium of claim 39, wherein the one or more programs further include instructions for:

prior to displaying the user interface that include the first representation of received atrial fibrillation data for the first time period and the first representation of received non-heart data for the first time period, displaying a second user interface that includes:

a third representation of received atrial fibrillation data for the first time period; and a second selectable user interface object; and wherein displaying the user interface occurs in response to receiving a second user input corresponding to the second selectable user interface object.

50. The non-transitory computer-readable storage medium of claim 39, wherein the received non-heart data of the first representation of received non-heart data for the first time period is data collected via one or more sensors.

51. The non-transitory computer-readable storage medium of claim 39, wherein the received non-heart data of the first representation of received non-heart data for the first time period is user-inputted data.

52. The non-transitory computer-readable storage medium of claim 39, wherein:

the first representation of received non-heart data for the first time period is a representation of a third type of received non-heart data; and the user interface includes a third representation of received non-heart data for the first time period that is a representation of a fourth type of received non-heart data different from the third type of received non-heart data.

53. The non-transitory computer-readable storage medium of claim 39, wherein the first representation of received non-heart data for the first time period is a data chart.

54. The non-transitory computer-readable storage medium of claim 39, wherein the one or more programs further include instructions for:

displaying a representation of a derived atrial fibrillation data value that is based, at least in part, on the received atrial fibrillation data for the first time period and received atrial fibrillation data for a fourth time period that is different than the first time period.

55. The non-transitory computer-readable storage medium of claim 54, wherein the one or more programs further include instructions for:

prior to displaying the representation of a derived atrial fibrillation data value, displaying an indication of progress towards collection of a quantity of atrial fibrillation data that is to be collected before displaying the representation of a derived atrial fibrillation data value.

56. The non-transitory computer-readable storage medium of claim 54, wherein the derived atrial fibrillation data value is a comparison of the received atrial fibrillation data for the first time period and the received atrial fibrillation data for the fourth time period.

57. The non-transitory computer-readable storage medium of claim 54, wherein the derived atrial fibrillation data value is based on a comparison of a recurring sub-period of time in the first time period and the fourth time period.

* * * * *